United States Patent
Hofmann et al.

(10) Patent No.: US 6,194,181 B1
(45) Date of Patent: Feb. 27, 2001

(54) FERMENTATIVE PREPARATION PROCESS FOR AND CRYSTAL FORMS OF CYTOSTATICS

(75) Inventors: Hans Hofmann, Ettingen (CH); Marion Mahnke, Steinen (DE); Klaus Memmert, Lörrach (DE); Frank Petersen, Weil am Rhein (DE); Thomas Schupp, Möhlin (CH); Ernst Küsters, Eschbach; Michael Mutz, Freiburg, both of (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/248,910

(22) Filed: Feb. 12, 1999

(30) Foreign Application Priority Data

Feb. 19, 1998 (CH) .................................................. 396/98
May 5, 1998 (CH) ................................................. 1007/98

(51) Int. Cl.⁷ ..................................................... C12P 17/16
(52) U.S. Cl. ............................................................. 435/118
(58) Field of Search .............................................. 435/118

(56) References Cited

U.S. PATENT DOCUMENTS

| | | | |
|---|---|---|---|
| 3,459,731 | 8/1969 | Gramera et al. | 260/209 |
| 4,383,992 | 5/1983 | Lipari | 424/238 |
| 4,535,152 | 8/1985 | Szeijtli et al. | 536/103 |
| 4,659,696 | 4/1987 | Hirai et al. | 514/15 |
| 5,496,804 | 3/1996 | Reed et al. | 514/12 |
| 5,565,478 | 10/1996 | Kohn et al. | 514/359 |
| 5,641,803 | 6/1997 | Carretta et al. | 514/449 |

FOREIGN PATENT DOCUMENTS

| | | |
|---|---|---|
| 1222697 | 6/1987 | (CA) . |
| 31 182 18 | 4/1982 | (DE) . |
| 33 170 64 | 11/1984 | (DE) . |
| 33 461 23 | 6/1985 | (DE) . |
| 41 38 042 | 5/1993 | (DE) . |
| WO 93/10121 | 5/1993 | (DE) . |
| 42 07 922 | 9/1993 | (DE) . |
| 0 094 157 | 11/1983 | (EP) . |
| 0 149 197 | 7/1985 | (EP) . |
| 0 197 571 | 10/1986 | (EP) . |
| 0 091 781 | 11/1986 | (EP) . |
| 0 292 050 | 11/1988 | (EP) . |
| 0 300 526 | 1/1989 | (EP) . |
| 0 320 032 | 6/1989 | (EP) . |
| 0 396 184 | 11/1990 | (EP) . |
| 0 499 322 | 8/1992 | (EP) . |
| 0 503 710 | 9/1992 | (EP) . |
| 0 636 634 | 2/1995 | (EP) . |
| 0 818 469 | 1/1998 | (EP) . |
| 2189245 | 10/1987 | (GB) . |
| WO90/12035 | 10/1990 | (WO) . |
| WO91/07967 | 6/1991 | (WO) . |
| WO91/11200 | 8/1991 | (WO) . |
| WO93/10121 | 5/1993 | (WO) . |
| WO93/19061 | 9/1993 | (WO) . |
| WO93/23017 | 11/1993 | (WO) . |
| WO 94/26728 | 11/1994 | (WO) . |
| WO95/08993 | 4/1995 | (WO) . |
| WO95/31178 | 11/1995 | (WO) . |
| WO96/14090 | 5/1996 | (WO) . |
| WO97/18839 | 5/1997 | (WO) . |
| WO97/19086 | 5/1997 | (WO) . |
| WO98/22461 | 5/1998 | (WO) . |
| WO98/25929 | 6/1998 | (WO) . |
| WO99/01124 | 1/1999 | (WO) . |
| WO 99/65913 | 12/1999 | (WO) . |

OTHER PUBLICATIONS

Bollag et al., Cancer Research, vol. 55, pp. 2325–2333 (1995).
Chemical Abstracts 98:124208s, Koho, JP 57,194,787, Nov. 30, 1982.
Chemical Abstracts 96:223270w, Koho, JP 8,224,312, Jan. 30, 1982.
Gerth et al., The Journal of Antibiotics, vol. 49, No. 6, pp. 560–562 (1996).
Hoefle et al., Angew. Chem., vol. 108, No. 13/14, pp. 1671–1673 (1996).
Horikoshi, Chemical Economy & Engineering Review, vol. 13, No. 1–2 (140–145) pp. 7–11 (1981).
Loftsson et al., Journal of Pharmaceutical Sciences, vol. 85, No. 10, pp. 1017–1025 (1996).
May, Scott et al., Chem. Commun. Total sysnthesis of (–) epothilone B, pp. 1597–1598 (1998).
Meng et al., J. Am Chem. Soc., vol. 119, pp. 10073–10092 (1997).
Nicolaou et al., J. Am. Chem. Soc., vol. 119, pp. 7974–7991 (1997).
Nicolaou et al., Nature, vol. 387, pp. 268–272 (1997).
Rajewski et al., Journal of Pharmaceutical Science, vol. 85, No. 11, pp. 1142–1169 (1996).
Rowinski, Ann. Rev. Med., vol. 48, pp. 353–374 (1997).

*Primary Examiner*—Herbert J. Lilling
(74) *Attorney, Agent, or Firm*—Michael U. Lee

(57) ABSTRACT

The invention relates to a new process for concentrating epothilones in culture media, a new process for the production of epothilones, a new process for separating epothilones A and B and a new strain obtained by mutagenesis for the production of epothilones, as well as aspects related thereto. New crystal forms of epothilone B are also described.

15 Claims, No Drawings

FERMENTATIVE PREPARATION PROCESS FOR AND CRYSTAL FORMS OF CYTOSTATICS

The invention relates to a new biotechnological preparation process that can be used on an industrial scale for the production of epothilones, especially a process for concentrating these compounds in the culture medium, as well as a new strain for the fermentative preparation of these compounds. The invention also relates to new crystal forms of epothilones, especially epothilone B, obtainable by the new processes, their usage in the production of pharmaceutical preparations, new pharmaceutical preparations comprising these new crystal forms and/or the use of these compounds in the treatment of proliferative diseases such as tumours, or in the production of pharmaceutical formulations which are suitable for this treatment.

BACKGROUND OF THE INVENTION

Of the existing cytotoxic active ingredients for treating tumours, Taxol® (Paclitaxel; Bristol-Myers Squibb), a microtubuli-stabilising agent, plays an important role and has remarkable commercial success. However, Taxol has a number of disadvantages. In particular, its very poor solubility in water is a problem. It therefore became necessary to administer Taxol® in a formulation with Cremophor EL® (polyoxyethylated castor oil; BASF, Ludwigshafen, Germany). Cremophor EL® has severe side effects; for example it causes allergies which in at least one case have led even to the death of a patient.

Although the Taxan class of microtubuli-stabilising anticancer agents has been commended as "perhaps the most important addition to the pharmaceutical armoury against cancer in the last decade" (see Rowinsky E. K., Ann. rev. Med. 48, 353–374 (1997)), and despite the commercial success of Taxol®, these compounds still do not appear to represent a really great breakthrough in the chemotherapy of cancer. Treatment with Taxol® is linked with a series of significant side effects, and a few primary classes of compact tumours, namely colon and prostate tumours, respond to this compound only to a small extent (see Rowinsky E. K., inter alia). In addition, the efficacy of Taxol can be impaired and even completely neutralised by acquired resistance mechanisms, especially those based on the overexpression of phosphoproteins, which act as efflux pumps for active ingredients, such as "Multidrug Resistance" due to overexpression of the multidrug transport glycoprotein "P-glycoprotein".

Epothilones A and B represent a new class of microtubuli-stabilising cytotoxic active ingredients (see Gerth, K. et al., J. Antibiot. 49, 560–3 (1966)) of the formulae:

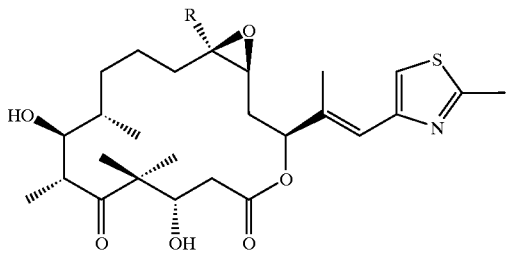

wherein R signifies hydrogen (epothilone A) or methyl (epothilone B).

These compounds have the following advantages over Taxol®:

a) They have better water-solubility and are thus more easily accessible for formulations.

b) It has been reported that, in cell culture experiments, they are also active against the proliferation of cells, which, owing to the activity of the P-glycoprotein efflux pump making them "multidrug resistant", show resistance to treatment with other chemotherapy agents including Taxol® (see Bolag, D. M., et al., "Epothilones, a new class of microtubuli-stabilizing agents with a Taxol-like mechanism of action", Cancer Research 55, 2325–33 (1995)). And c) it could be shown that they are still very effective in vitro against a Taxol®-resistant ovarian carcinoma cell line with modified β-tubulin (see Kowalski, R. J., et al., J. Biol. Chem. 272(4), 2534–2541 (1997)).

Pharmaceutical application of the epothilones, for example for tumour treatment, is possible in an analogous manner to that described for Taxol, see for example U.S. Pat. No. 5,641,803; U.S. Pat. No. 5,496,804; U.S. Pat. No. 5,565,478).

In order to be able to use the epothilones on a larger scale for pharmaceutical purposes, however, it is necessary to obtain appropriate amounts of these compounds.

Until now, the extraction of natural substances by means of myxobacteria, especially the epothilones from the cell strain *Sorangium cellulosum* Soce90 (deposited under no. 6773 at the German Collection of Microorganisms, see WO 93/10121) was described in literature. In order to obtain a satisfactory concentration of the natural substances, especially the epothilones, in the culture medium for the subsequent extraction, previously an adsorbate resin based on polystyrene was always added, for example Amberlite XAD-1180 (Rohm & Haas, Frankfurt, Germany).

However, the disadvantage of this process is that, on a large scale, it leads to an abundance of problems. Valves are impaired by the globules of resin, pipes can block, and apparatus may be subject to greater wear due to mechanical friction. The globules of resin are porous and therefore have a large inner surface area (about 825 $m^2$/gram resin). Sterilisation becomes a problem, as air enclosed in the resin is not autoclaved. Thus, the process cannot be practicably carried out on a large scale using resin addition.

On the other hand, without adding resin globules, a satisfactory concentration of epothilones cannot be achieved in the culture medium.

Surprisingly, the requirements for finding a way out of this dilemma have now been found, enabling a satisfactory concentration of natural substances to be obtained from microorganisms, in particular myxobacteria, which produce epothilones such as epothilone A or B, in particular a concentration of epothilones A and B, in the culture medium, without the addition of resins, and thus enabling production of these compounds, especially epothilones to be carried out on a technical and industrial scale without the above-mentioned disadvantages.

DETAILED DESCRIPTION OF THE INVENTION

One aspect of the invention relates to a process for concentrating epothilones, especially epothilone A and/or B, in particular epothilone B, in a culture medium, in order to produce these compounds on a biotechnological scale, the process comprising microorganisms which produce these compounds, especially myxobacteria (as producers of natural substances), whereby a complex-forming components which is soluble in the culture medium is added to the medium.

A further aspect relates to the corresponding culture medium, which comprises a corresponding complex-forming component and microorganisms, especially myxobacteria, in particular of the genus Sorangium, which are suitable for producing epothilones, especially epothilone A and/or B.

A further aspect of the invention relates to a process for the production of epothilones, especially epothilone A and/or B, especially the two pure compounds, in particular epothilone B, which is characterised in that the epothilones are obtained by working up a culture medium for the biotechnological preparation of these compounds, which comprises as producers of natural substances microorganisms, especially myxobacteria, that produce these compounds, and to which a complex-forming component that is soluble in the culture medium is added, and the subsequent purification and, if desired, separation of the epothilones, for example epothilone A and B.

A fourth aspect of the invention relates to a method of separating epothilones, especially epothilones A and B from one another, which is characterised by chromatography on a reversed-phase column with an eluant comprising a lower alkyl cyanide.

A further aspect of the invention relates to a strain of *Sorangium cellulosum* obtained by mutagenesis, which under otherwise identical conditions, produces more epothilones than *Sorangium cellulosum* Soce90.

A further aspect also relates to new crystal forms of epothilone B.

The general terms used hereinabove and hereinbelow preferably have the meanings given hereinbelow:

Where reference is made hereinabove and hereinbelow to documents, these are incorporated insofar as is necessary.

The prefix "lower" always indicates that the correspondingly named radical contains preferably up to a maximum of 7 carbon atoms, in particular up to 4 carbon atoms, and is branched or unbranched. Lower alkyl may be for example unbranched or branched once or more, and is e.g. methyl, ethyl, propyl such as isopropyl or n-propyl, butyl such as isobutyl, sec.-butyl, tert.-butyl or n-butyl, or also pentyl such as amyl or n-pentyl.

A culture medium for the biotechnological preparation of epothilones which contains microorganisms that produce these compounds, especially myxobacteria, as producers of natural substances, is primarily a medium which comprises a corresponding (naturally occurring or also obtainable by cultivation or in particular by genetic modification) microorganism, especially a myxobacterial strain which is in a position to produce these compounds, in particular a myxobacterium of the genus Sorangium, preferably (in particular for epothilone production) a microorganism of the type *Sorangium cellulosum* Soce90 (see WO 93/10121), or a biomaterial derived therefrom or from parts of this myxobacterium, especially a correspondingly derived strain, in particular the strain having the reference BCE33/10, in particular the strain having the reference BCE 63/114 or mutants thereof, and in addition, together with water, preferably other conventional and appropriate constituents of culture media, such as biopolymers, sugar, amino acids, salts, nucleic acids, vitamins, antibiotics, semiochemicals, growth media, extracts from biomaterials such as yeast or other cell extracts, soy meal, starch such as potato starch and/or trace elements, for example iron ions in complex-bound form, or suitable combinations of all or some of these constituents and/or also analogous additions. The corresponding culture media are known to the person skilled in the art or may be produced by known processes (see e.g. the culture media in the examples of the present disclosure, or in WO 93/10121).

One preferred myxobacterium is a strain selected by UV mutagenesis and selection for increased formation of epothilone A and/or B over *Sorangium cellulosum* Soce90, which is deposited in the DSM under no. 6773, especially the mutant BCE33/10, which was deposited under the number DSM 11999 on Feb. 9, 1998 at the German Collection of Microorganisms and Cell Cultures (DSMZ Mascheroder Weg 1b, D-38124, Braunschweig, Germany), and most preferably the mutant having the reference BCE 63/114, which was deposited under number DSM 12539 on Nov. 27, 1998 at the German Collection of Microorganisms and Cell Cultures (DSMZ).

Strain culture and morphological description of strain BCE 33/10 and of strain BCE 63/114: The strain can grow on cellulose as the sole source of carbon and energy with potassium nitrate as the sole source of nitrogen, e.g. on filter paper over ST21 mineral salt agar (0.1% $KNO_3$; 0.1% $MgSO_4 \times 7\ H_2O$; 0.1% $CaCl_2 \times 2\ H_2O$; 0.1% $K_2HPO_4$; 0.01% $MnSO_4 \times 7\ H_2O$; 0.02% $FeCl_3$; 0.002% yeast extract; standard trace element solution; 1% agar). On this medium, dark reddish-brown to blackish-brown fruiting bodies are formed. They consist of small sporangioles (ca. 15 to 30 µm diameter) and exist in dense heaps and packs of varying size.

The vegetative bacilli have the shape typical of Sorangium (relatively compact, under the phase contrast microscope dark, cylindrical bacilli with broad rounded ends, on average 3 to 6 µm long and 1 µm thick).

Epothilones are primarily epothilone A and/or B, but also other epothilones, for example epothilones C and D named in International Application WO 97/19086 and WO 98/22461, epothilones E and F named in WO 98/22461, and further epothilones obtainable from corresponding microorganisms.

A water-soluble complex-forming component is primarily a water-soluble oligo- or poly-peptide derivative or in particular an oligo- or polysaccharide derivative of cyclic or helical structure, which forms an intramolecular cavity, which because of its sufficiently hydrophobic properties is in a position to bind epothilones, especially epothilone A and/or epothilone B. A water-soluble complex-forming component that is especially preferred is one that is selected from cyclodextrins or (in particular) cyclodextrin derivatives, or mixtures thereof.

Cyclodextrins are cyclic (α-1,4)-linked oligosaccharides of α-D-glucopyranose with a relatively hydrophobic central cavity and a hydrophilic external surface area.

The following are distinguished in particular (the figures in parenthesis give the number of glucose units per molecule): α-cyclodextrin (6), β-cyclodextrin (7), γ- cyclodextrin (8), δ-cyclodextrin (9), ε-cyclodextrin (10), ζ-cyclodextrin (11), η-cyclodextrin (12), and θ-cyclodextrin (13). Especially preferred are δ-cyclodextrin and in particular α-cyclodextrin, β-cyclodextrin or γ-cyclodextrin, or mixtures thereof.

Cyclodextrin derivatives are primarily derivatives of the above-mentioned cyclodextrins, especially of α-cyclodextrin, β-cyclodextrin or γ-cyclodextrin, primarily those in which one or more up to all of the hydroxy groups (3 per glucose radical) are etherified or esterified. Ethers are primarily alkyl ethers, especially lower alkyl, such as methyl or ethyl ether, also propyl or butyl ether; the aryl-hydroxyalkyl ethers, such as phenyl-hydroxy-lower-alkyl, especially phenyl-hydroxyethyl ether; the hydroxyalkyl ethers, in particular hydroxy-lower-alkyl ethers, especially 2-hydroxyethyl, hydroxypropyl such as 2-hydroxypropyl or hydroxy-butyl such as 2-hydroxybutyl ether; the carboxyalkyl ethers, in particular carboxy-lower-alkyl ethers, especially carboxymethyl or carboxyethyl ether; derivatised carboxyalkyl ethers, in particular derivatised carboxy-lower-alkyl ether in which the derivatised carboxy is etherified or amidated carboxy (primarily aminocarbonyl, mono- or di-lower-alkyl-aminocarbonyl, morpholino-, piperidino-, pyrrolidino- or piperazino-carbonyl, or alkyloxycarbonyl), in particular lower alkoxycarbonyl-lower-alkyl ether, for example methyloxycarbonylpropyl ether or ethyloxycarbonylpropyl ether; the sulfoalkyl ethers, in particular sulfo-lower-alkyl ethers, especially sulfobutyl ether; cyclodextrins in which one or more OH groups are etherified with a radical of formula

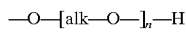

wherein alk is alkyl, especially lower alkyl, and n is a whole number from 2 to 12, especially 2 to 5, in particular 2 or 3; cyclodextrins in which one or more OH groups are etherified with a radical of formula

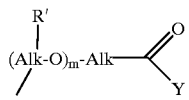

wherein R' is hydrogen, hydroxy, —O—(alk—O)$_z$—H, —O—(alk(—R)—O—)$_p$—H or —O—(alk(—R)—O—)$_q$—alk—CO—Y; alk in all cases is alkyl, especially lower alkyl; m, n, p, q and z are a whole number from 1 to 12, preferably 1 to 5, in particular 1 to 3; and Y is OR$_1$ or NR$_2$R$_3$, wherein R$_1$, R$_2$ and R$_3$ independently of one another, are hydrogen or lower alkyl, or R$_2$ and R$_3$ combined together with the linking nitrogen signify morpholino, piperidino, pyrrolidino or piperazine;
or branched cyclodextrins, in which etherifications or acetals with other sugars are present, especially glucosyl-, diglucosyl-(G$_2$-β-cyclodextrin), maltosyl- or dimaltosyl-cyclodextrin, or N-acetylglucosaminyl-, glucosaminyl-, N-acetylgalactosaminyl- or galactosaminyl- cyclodextrin.

Esters are primarily alkanoyl esters, in particular lower alkanoyl esters, such as acetyl esters of cyclodextrins.

It is also possible to have cyclodextrins in which two or more different said ether and ester groups are present at the same time.

Mixtures of two or more of the said cyclodextrins and/or cyclodextrin derivatives may also exist.

Preference is given in particular to α-, β- or γ-cyclodextrins or the lower alkyl ethers thereof, such as methyl-β-cyclodextrin or in particular 2,6-di-O-methyl-β-cyclodextrin, or in particular the hydroxy lower alkyl ethers thereof, such as 2-hydroxypropyl-α-, 2-hydroxypropyl-β- or 2-hydroxypropyl-γ-cyclodextrin.

The cyclodextrins or cyclodextrin derivatives are added to the culture medium preferably in a concentration of 0.02 to 10, preferably 0.05 to 5, especially 0.1 to 4, for example 0.1 to 2 percent by weight (w/v).

Cyclodextrins or cyclodextrin derivatives are known or may be produced by known processes (see for example U.S. Pat. No. 3,459,731; U.S. Pat. No. 4,383,992; U.S. Pat. No. 4,535,152; U.S. Pat. No. 4,659,696; EP 0 094 157; EP 0 149 197; EP 0 197 571; EP 0 300 526; EP 0 320 032; EP 0 499 322; EP 0 503 710; EP 0 818 469; WO 90/12035; WO 91/11200; WO 93/19061; WO 95/08993; WO 96/14090; GB 2,189,245; DE 3,118,218; DE 3,317,064 and the references mentioned therein, which also refer to the synthesis of cyclodextrins or cyclodextrin derivatives, or also: T. Loftsson and M. E. Brewster (1996): Pharmaceutical Applications of Cyclodextrins: Drug Solubilization and Stabilisation: Journal of Pharmaceutical Science 85 (10):1017–1025; R. A. Rajewski and V. J. Stella(1996): Pharmaceutical Applications of Cyclodextrins: In Vivo Drug Delivery: Journal of Pharmaceutical Science 85 (11): 1142–1169).

In the following description of the working up, "epothilone" is understood to be an epothilone which is obtainable from the corresponding microorganism, preferably epothilone C, D, E, F or especially A or in particular epothilone B. If not otherwise stated, where "epothilones" are mentioned, this is intended to be a general term which includes individual epothilones or mixtures.

Working up of the epothilones is effected by conventional methods; first of all, by separating a culture into the liquid phase (centrifugate or filtrate) and solid phase (cells) by means of filtration or centrifugation (tubular centrifuge or separator). The (main) part of the epothilones found in the centrifugate or in the filtrate is then directly mixed with a synthetic resin, for example a resin based on polystyrene as matrix (hereinafter referred to also simply as polystyrene resin), such as Amberlite XAD-16 [Rohm & Haas Germany GmbH, Frankfurt] or Diaion HP-20 [Resindion S.R.L., Mitsubishi Chemical Co., Milan] (preferably in a ratio of centrifugate: resin volume of ca. 10:1 to 100:1, preferably about 50:1). After a period of contact of preferably 0.25 to 50 hours, especially 0.8 to 22 hours, the resin is separated, for example by filtration or centrifugation. If required, after adsorption, the resin is washed with a strongly polar solvent, preferably with water. Desorption of the epothilones is then effected with an appropriate solvent, especially with an alcohol, in particular isopropanol. The solvent phase, especially the isopropanol phase, is then removed from the solvent, preferably by means of prior, simultaneous or subsequent addition of water, in particular in a circulating evaporator, thereby being concentrated if necessary, and the resulting water phase is extracted with a solvent suitable for forming a second phase, such as an ester, for example a lower alkanol lower alkanoate, typically ethyl acetate or isopropyl acetate. The epothilones are thereby transferred into the organic phase. Then the organic phase is concentrated to the extent necessary, preferably to dryness, for example using a rotary evaporator.

Subsequently, further processing takes place using the following steps, whereby the purification step by means of reversed-phase chromatography with elution with a nitrile is an inventive step and is thus compulsory, while the other steps are optional:
  molecular filtration (gel chromatography), e.g. on a column of material such as Sephadex LH-20 (Pharmacia, Uppsala, Sweden) with an alcohol such as methanol as eluant;
  separation of the epothilones by reversed-phase chromatography after being taken up in a suitable solvent, and elution with a mixture of nitrile/water (compulsory), preferably characterised in that the chromatography is carried out on a column of material, especially a RP-18 material, which is charged with hydrocarbon chains, such as hydrocarbon chains containing 18 carbon atoms, and an eluant comprising a nitrile, especially a lower alkyl-nitrile, in particular acetonitrile, is used, in particular a mixture of nitrile/water is used, especially a mixture of acetonitrile/water, preferably in a ratio of nitrile to water of about 1:99 to 99:1, primarily between 1:9 and 9:1, e.g. between 2:8 and 7:3, e.g. 3:7 or 4:6.

single or multiple extraction of the residue (especially after evaporation) in a two-phase system consisting of water and a solvent immiscible with water, preferably an ester, in particular a lower alkyl lower alkanoate, such as ethyl acetate or isopropyl acetate;

adsorption chromatography, in particular by adding to a column of silica gel and eluting with an appropriate solvent or solvent mixture, especially a mixture of ester/hydrocarbon, for example lower alkyl alkanoate/$C_4$–$C_{10}$-alkane, especially ethyl or isopropyl acetate/n-hexane, in which the ratio between the ester and hydrocarbon is preferably in the range 99:1 to 1:99, preferably 10:1 to 1:10, for example 4:1;

dissolving the residue, which may be obtained after concentration, in an appropriate solvent such as an alcohol, e.g. methanol;

mixing with activated carbon and removal thereof;

recrystallisation, e.g. from appropriate solvents or solvent mixtures, for example consisting of esters, ester/hydrocarbon mixtures or alcohols, especially ethyl or isopropyl acetate: toluene 1:10 to 10:1, preferably 2:3 (epothilone A) or methanol or ethyl acetate (epothilone B);

whereby between each step being employed, the resulting solutions or suspensions are concentrated if necessary, and/or liquid and solid components are separated from one another, in particular by filtering or centrifuging solutions/suspensions. The more precise definitions mentioned below can be preferably used in the above individual steps.

The further working up and purification is preferably carried out either by direct separation of the epothilones from one another by reversed-phase chromatography after being taken up in an appropriate solvent, for example a nitrile/water mixture, especially an acetonitrile/water mixture (ratio of nitrile to water 1:99 to 99:1, preferably 1:9 to 9:1, especially 3:1), if necessary after filtration or centrifugation, preferably on a silica gel that has been derivatized by hydrocarbon radicals, e.g. a silica gel modified by alkyl radicals containing 8 to 20, especially 18, C-atoms, eluting with an eluant comprising a nitrile, especially a lower alkylnitrile, such as acetonitrile, especially a mixture of the nitrile with water, such as an acetonitrile/water mixture, whereby detection of the interesting fractions is effected in conventional manner, for example by UV detection or (preferably) by on-line HPLC (HPLC with a very small column, the analyses taking less than 1 minute, and detection e.g. at 250 nm), this enabling a particularly exact separation of the fractions containing the desired product to take place; if required, with subsequent concentration, for example by distillation, to remove the nitrile; if desired, with subsequent single or multiple, for example double, extraction of the residue of evaporation in a two-phase system consisting of water and an immiscible solvent, such as ethyl acetate or isopropyl acetate; additional concentration of the organic phase and dissolving of the residue in an appropriate solvent, preferably an ester such as ethyl acetate or isopropyl acetate, if required, filtration or centrifugation, if desired adding to a column of silica gel and eluting with an appropriate solvent or solvent mixture, for example with a mixture of ester/hydrocarbon, e.g. lower alkyl alkanoate/$C_4$–$C_{10}$-alkane, especially ethyl or isopropyl acetate/n-hexane, in which the ratio of ester to hydrocarbon is preferably in the range 99:1 to 1:99, preferably 10:1 to 1:10, e.g. 4:1; subsequent combining of the fractions containing each desired epothilone, especially epothilone A or epothilone B, and after removing the solvent, for example by distillation, preferably concentrating to dryness; then, dissolving of the residue in an appropriate alcohol, preferably methanol; and if desired, in order to obtain especially high purity, mixing with activated carbon and then separating the activated carbon, for example by filtration; and finally, by recrystallisation as described below under variant 2 (for epothilone B in particular from methanol), separate extraction of the epothilones, especially epothilones A or B. This is the most preferred variant 1, the outstanding characteristic of which is the surprising direct separation by reversed-phase chromatography of the epothilone-containing mixture desorbed by the resin, despite all the impurities in the organic extract;

or (variant 2) first of all exclusion chromatography takes place (molecular filtration) e.g. on a column of material such as Sephadex LH-20 (Pharmacia, Uppsala, Sweden) with an alcohol such as methanol as eluant, and then subsequent separation of the epothilones present in the peak fractions obtained, e.g. epothilone A and B, by reversed-phase chromatography as described above for variant 1; if required twice, if peak fractions of one epothilone contain those of another, for example if those with epothilone A still contain residues of epothilone B; and then separate recrystallisation of each epothilone from appropriate solvents or solvent mixtures, for example from ethyl or isopropyl acetate-:toluene 1:10 to 10:1, preferably 2:3 (epothilone A) or methanol or ethyl acetate (epothilone B). This is variant 2 of working up and purification.

With variant 1, highly pure epothilone B may be obtained in a relatively simpler manner (the purity is preferably greater than 97%, especially over 99%).

Variant 1 preferably takes place as follows (whereby preferably the above-mentioned variants can be used instead of the following general definitions): First of all, a culture is separated into the liquid phase (centrifugate or filtrate) and a solid phase (cells) by means of filtration or centrifugation (tubular centrifuge or separator). The (main) part of the epothilones found in the centrifugate or filtrate is then directly mixed with a synthetic resin. After a contact period of preferably 0.25 to 50 hours, the resin is separated, for example by filtration or centrifugation. If required, after adsorption, the resin is washed with a strongly polar solvent, preferably with water. Desorption of the epothilones is then effected with an appropriate solvent, especially with an alcohol, in particular isopropanol. The solvent phase, especially isopropanol phase, is then removed from the solvent, preferably by means of prior, simultaneous or subsequent addition of water, in particular in a circulating evaporator, thereby being concentrated if necessary, and the resulting water phase is extracted with a solvent suitable for forming a second phase, such as an ester, for example a lower alkanol lower alkanoate, typically ethyl acetate or isopropyl acetate. The epothilones are then transferred into the organic phase. Then the organic phase is concentrated to the extent necessary, preferably to dryness, for example using a rotary evaporator. By subsequent reversed-phase chromatography on a silica gel derivatized with hydrocarbon atoms, e.g. a silica gel modified by alkyl radicals containing 18 C-atoms, and eluting with a mixture of a lower alkylnitrile such as acetonitrile with water, the epothilones are directly separated from one another, especially epothilone A and epothilone B;

then, concentration takes place by means of distillation, the residue is shaken out once or more, if desired from water with an appropriate solvent that is immiscible with water, preferably an ester such as isopropyl acetate, then the organic phase is again concentrated and the residue of evaporation is dissolved in an ester such as ethyl or isopropyl acetate, filtered if required, the filtrate added to a column of silica gel, and eluted with a mixture of ester/hydrocarbon, e.g. ethyl or isopropyl acetate/n-hexane; subsequently, the fractions containing the epothilone, especially epothilone A or B, are respectively combined and, after removing the solvent by distillation, concentrated, preferably to dryness; the residue is then dissolved in an appropriate lower alkanol, preferably methanol, and in order to obtain especially high purity, mixed with activated carbon and then filtered; finally, the epothilones are extracted by recrystallisation (in the case of epothilone B preferably from methanol).

Variant 2 is effected preferably as follows: After harvest, a culture is separated into the liquid phase (centrifugate) and solid phase (cells) by means of centrifugation (tubular centrifuge or separator). The main part of the epothilones are found in the centrifugate, which is then directly mixed with a polystyrene resin, such as Amberlite XAD-16 [Rohm & Haas Germany GmbH, Frankfurt] or Diaion HP-20 [Resindion S.R.L., Mitsubishi Chemical Co., Milan] (preferably in a ratio of centrifugate: resin volume of ca. 10:1 to 100:1, preferably about 50:1) and stirred in an agitator. In this step, the epothilones are transferred from the cyclodextrin to the resin. After a period of contact of ca. 1 hour, the resin is separated by centrifugation or filtration. Adsorption of the epothilones onto the resin may also be effected in a chromatography column, by placing the resin in the column and running the centrifugate over the resin. After adsorption, the resin is washed with water. Desorption of the epothilones from the resin is effected with isopropanol. The isopropanol phase is then freed of isopropanol preferably by the addition of water in particular in a circulating evaporator, and the resulting water phase is extracted with ethyl acetate. The epothilones are thus transferred from the water phase to the ethyl acetate phase. Then the ethyl acetate extract is concentrated to dryness, for example using a rotary evaporator. An initial concentration of the epothilones is then achieved by means of molecular filtration (e.g. Sephadex LH-20 [Pharmacia, Uppsala, Sweden] with methanol as eluant). The peak fractions from the molecular filtration contain epothilone A and B and have a total epothilone content of >10%. Separation of these peak fractions, which contain epothilone A and B in a mixture, into the individual components, then follows by means of chromatography on a "reversed-phase", e.g. RP-18 phase (phase which is modified by alkyl radicals containing 18 carbon atoms per chain), with an appropriate eluant, preferably one containing a nitrile such as acetonitrile (this gives better separation than for example alcohols such as methanol). Epothilone A elutes before epothilone B. The peak fractions with epothilone B may still contain small portions of epothilone A, which can be removed by further separation on RP-18. Finally, the epothilone A fraction is crystallised directly from ethyl acetate:toluene=2:3, and the epothilone B fraction from methanol or ethyl acetate.

Preferred Embodiment of the Invention

The invention preferably relates to a process for the concentration of epothilones, especially epothilone A and/or B, in particular epothilone B, in a culture medium for the biotechnological preparation of this (these) compound(s), which contains a microorganism which is suitable for this preparation, especially a Sorangium strain, especially of the type *Sorangium cellulosum* Soce90, or a mutant arising therefrom, in particular the strain having reference BCE 33/10, especially the strain having reference BCE 63/114, water and other usual appropriate constituents of culture media, whereby a cyclodextrin or a cyclodextrin derivative, or a mixture of two or more of these compounds is added to the medium, especially one or more, preferably one or two or more cyclodextrins selected from α-cyclodextrin (6), β-cyclodextrin (7), γ-cyclodextrin (8), δ-cyclodextrin (9), ε-cyclodextrin (10), ζ-cyclodextrin (11), η-cyclodextrin (12), and θ-cyclodextrin (13), especially α-cyclodextrin, β-cyclodextrin or γ-cyclodextrin; or primarily a cyclodextrin derivative or mixture of cyclodextrin derivatives selected from derivatives of a cyclodextrin, in which one or more up to all of the hydroxy groups are etherified to an alkyl ether, especially lower alkyl, such as methyl or ethyl ether, also propyl or butyl ether; an aryl-hydroxyalkyl ether, such as phenyl-hydroxy-lower-alkyl, especially phenyl-hydroxyethyl ether; a hydroxyalkyl ether, in particular hydroxy-lower-alkyl ethers, especially 2-hydroxyethyl, hydroxypropyl such as 2-hydroxypropyl or hydroxybutyl such as 2-hydroxybutyl ether; a carboxyalkyl ether, in particular carboxy-lower-alkyl ether, especially carboxymethyl or carboxyethyl ether; a derivatised carboxyalkyl ether, in particular a derivatised carboxy-lower-alkyl ether in which the derivatised carboxy is aminocarbonyl, mono- or di-lower-alkyl-aminocarbonyl, morpholino-, piperidino-, pyrrolidino- or piperazino-carbonyl, or alkyloxycarbonyl, in particular lower alkoxycarbonyl, such as preferably lower alkoxycarbonyl-lower-alkyl ether, for example methyloxycarbonylpropyl ether or ethyloxycarbonylpropyl ether; a sulfoalkyl ether, in particular sulfo-lower-alkyl ether, especially sulfobutyl ether; a cyclodextrin in which one or more OH groups are etherified with a radical of formula $$-O-[alk-O-]_n-H$$

wherein alk is alkyl, especially lower alkyl, and n is a whole number from 2 to 12, especially 2 to 5, in particular 2 or 3; a cyclodextrin in which one or more OH groups are etherified with a radical of formula $$(Alk-O)_m-Alk-\overset{R'}{\underset{}{\diagup}}\overset{O}{\underset{Y}{\diagdown}}$$

wherein R' is hydrogen, hydroxy, $-O-(alk-O)_z-H$, $-O-(Alk(-R)-O-)_p-H$ or $-O-(alk(-R)-O-)_q-alk-CO-Y$; alk in all cases is alkyl, especially lower alkyl; m, n, p, q and z are a whole number from 1 to 12, preferably 1 to 5, in particular 1 to 3; and Y is $OR_1$ or $NR_2R_3$, wherein $R_1$, $R_2$ and $R_3$ independently of one another, are hydrogen or lower alkyl, or $R_2$ and $R_3$ combined together with the linking nitrogen signify morpholino, piperidino, pyrrolidino or piperazino; or a branched cyclodextrin, in which etherifications or acetals with other sugars are present, and which are selected from glucosyl-, diglucosyl-($G_2$-β-cyclodextrin), maltosyl- or dimaltosyl-cyclodextrin, or N-acetylglucosaminyl-, glucosaminyl-, N-acetylgalactosaminyl- and galactosaminyl-cyclodextrin; or a lower alkanoyl, such as acetyl ester of a cyclodextrin.

Particular preference is given to a process in which the cyclodextrin and/or the cyclodextrin derivative is added to the culture medium in a concentration of 0.02 to 10, preferably 0.005 to 10, more preferably 0.05 to 5, most preferably 0.1 to 4, for example 0.1 to 2, percent by weight (w/v).

Especially preferred is a process according to one of the two previous paragraphs, in which the cyclodextrin derivative is selected from a cyclodextrin, especially β-cyclodextrin, and a hydroxy lower alkyl-cyclodextrin, especially 2-hydroxypropyl-α-, -β- or -γ-cyclodextrin; or mixtures of one or more thereof; whereby 2-hydroxypropyl-β-cyclodextrin on its own is preferred in particular.

The invention also relates in particular to a culture medium, which comprises a cyclodextrin, a cyclodextrin derivative or a mixture of two or more complex-forming components selected from cyclodextrins and cyclodextrin derivatives, especially a cyclodextrin or cyclodextrin derivative as defined in the third-last paragraph, in particular as in the second-last paragraph, or a mixture of one or more of these compounds, and a microorganism which is suitable for producing epothilones, especially epothilone A and/or B, preferably a strain from the genus Sorangium, especially a strain of *Sorangium cellulosum*, e.g. the strain Soce90 or a mutant arising therefrom, in particular the strain BCE 33/10, or especially BCE 63/114.

A further aspect of the invention relates to a process for the production of epothilone A and/or B, especially the two pure compounds, in particular epothilone B, which is characterised in that the epothilones are separated for example by centrifugation into the solid and the liquid phase (centrifugate) by working up a culture medium for the biotechnological preparation of these compounds, as described above, to which has been added a complex-forming component which is soluble in the culture medium, in particular a cyclodextrin, a cyclodextrin derivative or a mixture of two or more cyclodextrins and/or cyclodextrin derivatives; the centrifugate is mixed with a resin, especially a polystyrene resin, or is run through a column filled with such a resin; if necessary, the resin is washed with water; the epothilone(s) is or are desorbed from the resin using a polar solvent, especially an alcohol, primarily a lower alkanol such as isopropanol; if necessary, concentrated by means of prior, simultaneous or subsequent addition of water; an organic solvent which is immiscible with water, for example an ester, such as ethyl acetate, is added, and the epothilone(s) is or are transferred to the organic phase, for example by agitating or stirring; where necessary, the organic phase is concentrated; the epothilones from the organic solution obtained are concentrated through a molecular sieve for compounds of low molecular weight; and then the fractions containing the epothilones, especially epothilone A and/or B undergo separation by a reversed-phase column, preferably eluting with an eluant containing a nitrile, such as acetonitrile (or instead, an eluant containing an alcohol, such as methanol); whereby epothilones A and B are extracted separately, and if desired, can be further concentrated by recrystallisation.

One preferred aspect of the invention relates to a process for the production of epothilone A and/or B, especially the two pure compounds, in particular epothilone B, which is characterised in that the epothilones are separated for example by centrifugation into the solid and the liquid phase (centrifugate) by working up a culture medium for the biotechnological preparation of these compounds, as described above, to which has been added a complex-forming component which is soluble in the culture medium, in particular a cyclodextrin, a cyclodextrin derivative or a mixture of two or more cyclodextrins and/or cyclodextrin derivatives; the centrifugate is mixed with a resin, especially a polystyrene resin, or is run through a column filled with such a resin; if necessary, the resin is washed with water; the epothilone(s) is or are desorbed from the resin using a polar solvent, especially an alcohol, primarily a lower alkanol such as isopropanol; if necessary, the polar solvent is removed by means of prior, simultaneous or subsequent addition of water; the resulting water phase is extracted with a solvent which is suitable for forming a second phase, for example an ester, such as diethyl ester, if necessary, the organic phase is concentrated, preferably to dryness; epothilone A and B are separated from one another directly by reversed-phase chromatography, eluting with an eluant containing a nitrile, especially a lower alkylnitrile, such as acetonitrile, whereby detection is effected in the usual manner, for example by UV detection or preferably by on-line HPLC (HPLC with a very small column, the analyses taking less than 1 minute, and detection e.g. at 250 nm); subsequent concentration, for example by distillation; if desired, the residue is treated from an aqueous solution once or more (for example twice) by extraction with a solvent which is immiscible with water, such as an ester; dissolved in an appropriate solvent, preferably an ester such as ethyl or isopropyl acetate, filtered if necessary, added to a column of silica gel and eluted with an appropriate solvent or solvent mixture, for example with an ester/hydrocarbon mixture; and subsequently, the fractions containing either epothilone A or especially B are separately combined and, after removing the solvent, for example by distillation, concentrated preferably to dryness; then the residue is dissolved in an appropriate alcohol, preferably methanol, then if desired, in order to obtain especially high purity, treated with activated carbon and then filtered; and finally epothilone A or B is obtained by recrystallisation (in the case of epothilone B, particularly from methanol).

A further preferred aspect of the invention relates to a method of separating epothilones, especially epothilones A and B from one another, which is characterised by chromatography on a reversed-phase column with an eluant containing a lower alkyl cyanide, chromatography being carried out on a column material, especially an RP-18 material, which is charged with hydrocarbon chains containing 18 carbon atoms, and employing an eluant containing a nitrile, especially a lower alkylnitrile, in particular acetonitrile, especially a mixture of nitrile/water, in particular a mixture of acetonitrile/water, preferably in a ratio of nitrile to water of ca. 1:99 to 99:1, primarily 1:9 to 9:1, e.g. between 2:8 and 7:3, e.g. 3:7 or 4:6. This separation may follow on to a filtration with a molecular sieve, or is preferably effected directly using the residue after adsorption of the epothilones from the culture medium containing a complex-forming component onto a resin, as described above ("variant 1") One advantage of separation with an eluant containing a lower alkylcyanide over that using alcohols, such as methanol, is the better separation of epothilones A and B.

The invention relates preferably to a process for the preparation of epothilones, which a) comprises a process for the concentration of epothilones, especially epothilone A and/or B, in particular epothilone B, in a culture medium for the biotechnological preparation of this (these) compound (s), which contains a microorganism which is suitable for this preparation, especially a Sorangium strain, especially of the type *Sorangium cellulosum* Soce90, or a mutant arising therefrom, in particular the strain having reference BCE 33/10, especially the strain having reference BCE 63/114, water and other usual appropriate constituents of culture media, whereby a cyclodextrin or a cyclodextrin derivative, or a mixture of two or more of these compounds is added to the medium, especially one or more, preferably one or two or more cyclodextrins selected from α-cyclodextrin (6), β-cyclodextrin (7), γ-cyclodextrin (8), δ-cyclodextrin (9), ε-cyclodextrin (10), ζ-cyclodextrin (11), η-cyclodextrin (12), and θ-cyclodextrin (13), especially α-cyclodextrin, β-cyclodextrin or γ-cyclodextrin; or primarily a cyclodextrin derivative or mixture of cyclodextrin derivatives selected from derivatives of a cyclodextrin, in which one or more up to all of the hydroxy groups are etherified to an alkyl ether, especially lower alkyl, such as methyl or ethyl ether, also propyl or butyl ether; an aryl-hydroxyalkyl ether, such as phenyl-hydroxy-lower-alkyl, especially phenyl-hydroxyethyl ether; a hydroxyalkyl ether, in particular hydroxy-lower-alkyl ether, especially 2-hydroxyethyl, hydroxypropyl such as 2-hydroxypropyl or hydroxybutyl such as 2-hydroxybutyl ether; a carboxyalkyl ether, in particular carboxy-lower-alkyl ether, especially carboxymethyl or carboxyethyl ether; a derivatised carboxyalkyl ether, in particular a derivatised carboxy-lower-alkyl ether in which the derivatised carboxy is aminocarbonyl, mono- or di-lower-alkyl-aminocarbonyl, morpholino-, piperidino-, pyrrolidino- or piperazinocarbonyl, or alkyloxycarbonyl, in particular lower alkoxycarbonyl, such as preferably a lower alkoxycarbonyl-lower-alkyl ether, for example methyloxy-carbonylpropyl ether or ethyloxy-carbonylpropyl ether; a sulfoalkyl ether, in particular sulfo-lower-alkyl ether, especially sulfobutyl ether; a cyclodextrin in which one or more OH groups are etherified with a radical of formula

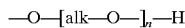

wherein alk is alkyl, especially lower alkyl, and n is a whole number from 2 to 12, especially 2 to 5, in particular 2 or 3; a cyclodextrin in which one or more OH groups are etherified with a radical of formula

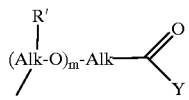

wherein
R' is hydrogen, hydroxy, —O—(alk—O)$_z$—H, —O—(Alk(—R)—O—)$_p$—H or
—O—(alk(—R)—O—)$_q$—alk—CO—Y; alk in all cases is alkyl, especially lower alkyl; m, n, p, q and z are a whole number from 1 to 12, preferably 1 to 5, in particular 1 to 3; and Y is OR$_1$ or NR$_2$R$_3$, wherein R$_1$, R$_2$ and R$_3$ independently of one another, are hydrogen or lower alkyl, or R$_2$ and R$_3$ combined together with the linking nitrogen signify morpholino, piperidino, pyrrolidino or piperazino;
or a branched cyclodextrin, in which etherifications or acetals with other sugars are present, and which are selected from glucosyl-, diglucosyl-(G$_2$-β-cyclodextrin), maltosyl- or di-maltosyl-cyclodextrin, or N-acetylglucosaminyl-, glucosaminyl-, N-acetylgalactosaminyl- and galactosaminyl-cyclodextrin; or a lower alkanoyl, such as acetyl ester of a cyclodextrin; and
b) comprises a step for separating the epothilones, especially epothilones A and B, from one another, which is characterised by chromatography on a reversed-phase column with an eluant containing a lower alkylcyanide, the chromatography being carried out on a column material, especially an RP-18 material, which is charged with hydrocarbon chains containing 18 carbon atoms, and employing an eluant containing a lower alkyinitrile, especially acetonitrile, in particular a mixture of lower alkylnitrile/water, preferably a mixture of acetonitrile/water, preferably in a ratio of lower alkylnitrile to water of ca. 1:99 to 99:1, primarily 1:9 to 9:1, e.g. between 2:8 and 7:3, e.g. 3:7 or 4:6, whereby if desired, it is possible to use further steps for working up and purification.

The invention also relates in particular to a mutant derived from the strain *Sorangium cellulosum* Soce90, especially a strain of *Sorangium cellulosum* which is obtainable by mutagenesis, preferably by one or more UV-induced mutagenesis steps (in particular by UV radiation in the range 200 to 400, especially 250 to 300 nm) with subsequent searching in each step for mutants having increased epothilone production (in particular increased epothilone concentration in the culture medium), this strain under otherwise identical conditions producing more epothilones, in particular more epothilone A and/or B, especially epothilone B, than *Sorangium cellulosum* Soce90, especially the *Sorangium cellulosum* strain BCE 33/10, in particular BCE 114.

The invention relates in particular to the individual process steps named in the examples or any combination thereof, the culture media named therein, crystal forms and the strain described therein.

The invention also relates to new crystal forms of epothilone B, especially a crystal form of epothilone B described as modification B and in particular described as modification A.

The crystal forms can be distinguished in particular by their X-ray diagrams. X-ray diagrams taken with a diffractometer and using Cu-Kα$_1$-radiation are preferably used to characterize solids of organic compounds. X-ray diffraction diagrams are used particularly successfully to determine the crystal modification of a substance. To characterize the existing crystal modification A and crystal modification B of epothilone B, the measurements are made at an angle range (2θ) of 2° and 35° with samples of substance that are kept at room temperature.

The X-ray diffraction diagram thus determined (reflection lines and intensities of the most important lines) from crystal modification A (modification A) of epothilone B is characterized by the following table.

| 2θ | Intensity |
|---|---|
| 7.7 | very strong |
| 10.6 | weak |
| 13.6 | average |
| 14.4 | average |
| 15.5 | average |
| 16.4 | weak |
| 16.8 | weak |
| 17.1 | weak |
| 17.3 | weak |
| 17.7 | weak |
| 18.5 | weak |
| 20.7 | strong |
| 21.2 | strong |
| 21.9 | weak |
| 22.4 | weak |
| 23.3 | strong |
| 25.9 | average |
| 31.2 | weak |
| 32.0 | average |

The invention also relates in particular to a new crystal form of epothilones B, which is characterised by a melting point of more than 120° C., especially between 120° C. and 128° C., in particular 124–125° C. Surprisingly, this value is considerably higher than the values previously described in literature. The invention relates especially to a crystal form of epothilone B, which is characterised by the X-ray diffraction diagram of the crystal form A and a melting point of above 120° C., especially between 120° C. and 128° C., for example between 124° C. and 125° C.

The X-ray diffraction diagram thus determined (reflection lines and intensities of the most important lines) of crystal modification B (modification B) of epothilone B is characterized by the following table.

| 2θ | Intensity |
|---|---|
| 6.9 | very strong |
| 8.0 | weak |
| 8.3 | average |
| 10.8 | strong |
| 11.5 | average |
| 12.4 | weak |
| 13.1 | strong |
| 15.5 | weak |
| 16.2 | weak |
| 16.7 | average |
| 18.1 | average |
| 18.6 | average |
| 20.4 | weak |
| 20.9 | strong |
| 21.3 | weak |
| 21.5 | very weak |
| 22.5 | average |
| 24.2 | weak |
| 25.1 | average |

The invention also relates in particular to a new crystal form of epothilones B, which is characterised by a melting point of more than 120° C., especially between 124 and 125° C. Surprisingly, this value is considerably higher than the values previously described in literature.

The new crystal forms are especially stable, particularly crystal form A, and they are therefore suitable as active ingredients for solid forms of administration, for storing in solid form or as intermediates (with particularly good storability) in the preparation of solid or liquid forms of administration.

The invention also relates to the use of the new crystal forms, especially crystal form B, but primarily crystal form A (all referred to hereinafter as active ingredient) in the production of pharmaceutical preparations, new pharmaceutical preparations which contain these new crystal forms, and/or the use of these compounds in the treatment of proliferative diseases, such as tumours. In the following, where pharmaceutical preparations or compositions which comprise or contain the active ingredient are mentioned, in the case of liquid compositions or compositions which no longer contain the crystal form as such, this is always understood to mean also the pharmaceutical preparations obtainable using the crystal forms (for example infusion solutions obtained using crystal forms A or B of epothilone B), even if they no longer contain the respective crystal form (for example because they exist in solution).

The invention also relates especially to the use of a new crystal form of epothilone B, especially the crystal form B or in particular crystal form A, in the production of pharmaceutical preparations, characterised by mixing a new crystal form of epothilone B with one or more carriers.

The invention also relates to a method of treating warm-blooded animals suffering from a proliferative disease, characterised by administering a dose of epothilone B which is effective for treating said disease in one or the new crystal forms to a warm-blooded animal requiring such treatment, also including in particular the treatment with those preparations that are produced using one of the new crystal forms.

To produce the pharmaceutical preparations, the active ingredient may be used for example in such a way that the pharmaceutical preparations contain an effective amount of the active ingredient together or in a mixture with a significant amount of one or more organic or inorganic, liquid or solid, pharmaceutically acceptable carriers.

The invention also relates to a pharmaceutical composition which is suitable for administration to a warm-blooded animal, especially humans, in the treatment of a proliferative disease, such as a tumour, the composition containing an amount of active ingredient that is suitable for treating said disease, together with a pharmaceutically acceptable carrier.

The pharmaceutical compositions according to the invention are those intended for enteral, especially nasal, rectal or oral, or preferably parenteral, especially intramuscular or intravenous administration to warm-blooded animals, especially humans, and they contain an effective dose of the active ingredient on its own or together with a significant amount of a pharmaceutically acceptable carrier. The dose of the active ingredient is dependent on the type of warm-blooded animal, the body weight, the age and the individual condition, individual pharmacokinetic situations, the disease to be treated and the type of administration.

The pharmaceutical compositions contain ca. 0.0001% to ca. 95%, preferably 0.001% to 10% or 20% to ca. 90% of active ingredient. Pharmaceutical compositions according to the invention may be present for example in unit dose forms, such as in the form of ampoules, vials, suppositories, dragées, tablets or capsules.

The pharmaceutical compositions according to the present invention are produced by known processes, for example by conventional dissolving, lyophilizing, mixing, granulating or manufacturing processes.

Solutions of the active ingredient, also suspensions, and in particular aqueous solutions or suspensions, are preferably employed, whereby it is also possible, for example in the case of lyophilised compositions which contain the active ingredient on its own or together with a pharmaceutically acceptable carrier, for example mannitol, for the solutions or suspensions to be prepared prior to administration. The pharmaceutical compositions may be sterilised and/or may contain excipients, for example preservatives, stabilisers, moisture-retaining agents and/or emulsion-forming agents, dissolving aids, salts for regulating osmotic pressure and/or buffers, and they are produced by known processes, for example by conventional dissolving or lyophilising processes. The solutions or suspensions mentioned may comprise viscosity-increasing substances, such as sodium carboxymethylcellulose, carboxymethylcellulose, dextran, polyvinylpyrrolidone or gelatin.

Suspensions in oil contain as the oil component vegetable oils, synthetic oils or semi-synthetic oils, which are customary for injection purposes. Notable examples are in particular liquid fatty acid esters, which contain as the acid component a long-chained fatty acid with 8 to 22, especially 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcoholic component of these fatty acid esters preferably has a maximum of 6 carbon atoms and is a mono- or polyhydroxy alcohol, for example a mono-, di- or tri-hydroxy alcohol, for example methanol, ethanol, propanol, butanol or pentanol, or an isomer thereof, but especially glycol and glycerol. The following examples of fatty acid esters may be mentioned in particular: propyl myristate, isopropyl palmitate, "Labrafil M 2375" (polyoxyethylene glycerol trioleate, Gattefossé, Paris), "Miglyol 812" (triglyceride of saturated fatty acids having a chain length of 8 to 12 carbon atoms, Hüls AG, Germany), but in particular vegetable oils such as cottonseed oil, almond oil, olive oil, castor oil, sesame oil, soybean oil and in particular peanut oil.

The injection or infusion preparations are produced according to customary methods under sterile conditions; the same applies also to the filling of the compositions into ampoules or vials and sealed containers.

Preference is given to an infusion solution which contains the active ingredient and a pharmaceutically acceptable organic solvent.

The pharmaceutically acceptable organic solvents which may be used in a formulation according to the invention can be selected from all such solvents which are familiar to a person skilled in the art. The solvent is preferably selected from an alcohol, e.g. absolute ethanol, ethanol/water mixtures, preferably 70% ethanol, polyethylene glycol 300, polyethylene glycol 400, polypropylene glycol and N-methylpyrrolidone, especially polypropylene glycol or 70% ethanol.

Particular preference is given to a formulation in pure polyethylene glycol, which is diluted prior to infusion in an appropriate solution, such as physiological saline.

The active ingredient is present in the formulation in a concentration of 0.001 to 100 mg/ml, preferably from ca. 0.05 to 5 mg/ml, or from 5 to 50 mg/ml.

Formulations of this type are easily stored as vials or ampoules. The vials or ampoules are typically made of glass, e.g. boron silicate. The vials or ampoules may be appropriate for any volume which is known from the prior art. They are preferably of sufficient size to be able to accept 0.5 to 5 ml of the formulation.

Prior to administration, the formulations have to be diluted in an aqueous medium suitable for intravenous administration before the active ingredient can be administered to patients.

It is preferable for the infusion solution to have the same or basically the same osmotic pressure as body fluids. Consequently, the aqueous medium contains an isotonic agent which has the effect of rendering the osmotic pressure of the infusion solution the same or basically the same as the osmotic pressure of body fluids.

The isotonic agent can be selected from all agents that are familiar to a person skilled in the art, for example mannitol, dextrose, glucose and sodium chloride. The isotonic agent is preferably glucose or sodium chloride. The isotonic agents may be used in quantities which impart the same or basically the same osmotic pressure to the infusion solution as body fluids. The exact quantities required can be determined by routine experiments and depend on the composition of the infusion solution and the type of isotonic agent.

The concentration of isotonizing agent in the aqueous medium depends on the type of each agent used. If glucose is used, it is preferably used in a concentration of 1 to 5% w/v, preferably 5% w/v. If the isotonizing agent is sodium chloride, it is preferably used in quantities of up to 1%, preferably ca. 0.9% w/v.

The infusion solution can be diluted with the aqueous medium. The amount of aqueous medium used is chosen according to the desired concentration of active ingredient in the infusion solution. The infusion solution is preferably produced by mixing a vial or an ampoule containing the infusion concentrate (see above) with an aqueous medium, so that a volume of between 200 ml and 1000 ml is attained with the aqueous medium. Infusion solutions may contain other additives that are normally used in formulations for intravenous administration. These additives also include antioxidants.

Antioxidants may be used to protect the active ingredient from degradation by oxidation. Antioxidants may be selected from those which are familiar to the person skilled in the art and which are suitable for intravenous formulations. The amount of antioxidant can be determined by routine experiments. As an alternative to adding an antioxidant, or additionally thereto, the antioxidant effect can be achieved by restricting the oxygen (air) contact with the infusion solution. This can be achieved in a simple way, by treating the vessel containing the infusion solution with an inert gas, e.g. nitrogen or argon.

Infusion solutions can be produced by mixing an ampoule or a vial with the aqueous medium, e.g. a 5% glucose solution in WFI in an appropriate container, e.g. an infusion bag or an infusion bottle.

Containers for the infusion solutions may be selected from conventional containers that are non-reactive with the infusion solution. Among those suitable are glass containers, especially of boron silicate, but plastic containers such as plastic infusion bags, are preferred.

Plastic containers may also be made of thermoplastic polymers. The plastic materials may also contain additives, e.g. softeners, fillers, antioxidants, antistatic agents or other customary additives.

Suitable plastics for the present invention should be resistant to elevated temperatures used for sterilisation. Preferred plastic infusion bags are the PVC materials which are known to the person skilled in the art.

A large range of container sizes may be considered. When selecting the size of the container, the factors to be taken into consideration are especially the solubility of epothilones in an aqueous medium, easy handling, and if appropriate, storage of the container. It is preferable to use containers which hold between ca. 200 and 1000 ml of infusion solution.

Owing to their good formulating properties, the new crystal forms of epothilone B according to the invention are especially suitable for the simple and reproducible production of the said infusion solutions. However, the new crystal forms are especially suitable for the production of pharmaceutical formulations which contain the active ingredient in solid form, for example oral formulations.

Pharmaceutical formulations for oral application may be obtained by combining the active ingredient with solid carriers, if desired by granulating the resultant mixture, and further processing the mixture, if desired or if necessary, after adding suitable adjuvants, into tablets, dragée cores or capsules. It is also possible to embed them in plastic substrates which enable the active ingredient to be diffused or released in measured quantities.

Suitable pharmaceutically employable carriers are especially fillers, such as lactose, saccharose, mannitol or sorbitol, cellulose preparations, and/or calcium phosphates, for example tricalcium phosphate or calcium hydrogen phosphate, and binders, such as starches, for example maize, wheat, rice or potato starch, gelatin, tragacanth, methyl cellulose, hydroxypropyl methyl cellulose, sodium carboxymethylcellulose, and/or polyvinyl pyrrolidone, and/or, if desired, disintegrators, such as the above-mentioned starches, crosslinked vinylpyrrolidones, agar, alginic acid or a salt thereof, such as sodium alginate. Adjuvants are in particular flow-improving agents and lubricants, e.g. silicates, talcum, stearic acid or salts thereof, such as magnesium or calcium stearate and/or polyethylene glycol. Dragée cores are provided, if desired, with appropriate gastric-juice-resistant coatings, using inter alia concentrated sugar solutions, gum arabic, talcum, polyvinyl pyrrolidone, polyethylene glycol and/or titanium dioxide, or coating solutions in suitable organic solvents, or in order to produce gastric-juice-resistant coatings, solutions of appropriate cellulose preparations, such as ethyl cellulose phthalate or hydroxypropyl methyl cellulose phthalate. Capsules are dry capsules consisting of gelatin or pectin, and if required, a softener such as glycerol or sorbitol. The dry capsules may contain the active ingredient in the form of granules, for example with fillers, such as lactose, binders, such as starches, and/or lubricants, such as talc or magnesium stearate, and where appropriate stabilizers. In soft capsules, the active ingredient may be present in dissolved or preferably suspended form, whereby oily adjuvants such as fat oils, paraffin oil or liquid propylene glycols are added; stabilizers and/or antibacterial additives may also be added. Dyes or pigments can be added to the tablets or dragée coatings, for example to improve identification or to distinguish different dosages of active ingredient.

The usage in the treatment of a proliferative disease with one of the crystal forms B and in particular A preferably takes place whereby the crystal form (preferably as for the usage in the preparation of an infusion solution, as described above) is administered to a warm-blooded animal, especially a human, in a dose which can be determined at between 20 and 133%, preferably between 25 and 100%, of the Maximum Tolerated Dose (MTD) by standard methods, for example using a modified Fibronacci series, in which the increases in dosages for successive amounts are 100%, 67%, 50% and 40% followed by 33% for all subsequent doses; and, if necessary, one or more further doses administered in the dosage range given above for the first dose, each dose after a period of time which allows sufficient recovery of the individual being treated after the preceding administration, in particular one week or more after the first administration, preferably 2 to 10 weeks, especially 3 to 6 weeks after each preceding administration. In general, this treatment scheme, in which a high dosage is administered once, twice or several times with sufficiently long intervals between the individual administrations for recovery to take place, is preferred over a more frequent treatment with lower doses, since hospitalisation is less frequent and for a shorter period and an improved anti-tumour effect can be expected. The dosage of epothilone B for humans is preferably between 0.1 and 50 mg/m$^2$, preferably between 0.2 and 10 mg/m$^2$.

The following Examples serve to illustrate the invention without limiting its scope.

Caution: When handling epothilones, appropriate protective measures must be taken, where necessary, in view of their high toxicity.

The 750 and 5000 liter fermenters used in the following are refined steel fermenters from the company Alpha AG, Nidau, Switzerland.

EXAMPLE 1
Preparation of the Strain BCE33/10 and the Strain BCE63/114 By Means of Mutation and Selection The strain employed is the mutant BCE33/10 (deposited at the German Collection of Microorganisms and Cell Cultures under number DSM 11999 on Feb. 9, 1998) or the mutant BCE63/114 (deposited at the German Collection of Microorganisms and Cell Cultures under number DSM 12539 on Nov. 27, 1998), which is derived from the strain *Sorangium cellulosum* Soce90 by mutation and selection as described below. In liquid media, the mutant BCE33/10, as well as BCE63/114, forms bacilli typical of Sorangia, with rounded ends and a length of 3–6 μm, as well as a width of ca. 1 μm. *Sorangium cellulosum* Soce90 was obtained from the German Collection of Microorganisms under number DSM 6773.

Preparation of the mutant BCE33/10 comprises three mutation steps with UV light and selections of individual colonies. The procedure in detail is carried out in accordance with the following operating steps.

Cultivation From the Ampoule

The cells of the DSM6773 ampoule are transferred to 10 ml of G52 medium in a 50 ml Erlenmeyer flask and incubated for 6 days in an agitator at 30° C. and at 180 rpm. 5 ml of this culture are transferred to 50 ml of G52 medium (in a 200 ml Erlenmeyer flask) and incubated at 180 rpm for 3 days in an agitator at 30° C.

First UV Mutation Step and Selection

Portions of 0.1 ml of the above culture are plated out onto several Petri dishes containing agar medium S42. The plates are then each exposed to UV light (maximum radiation range of 250–300 nm) for 90 or 120 seconds at 500 μwatt per cm$^2$. The plates are then incubated for 7–9 days at 30° C., until individual colonies of 1–2 mm are obtained. The cells of 100–150 colonies are then each plated out from an individual colony by means of a plastic loop in sectors onto Petri dishes containing S42 agar (4 sectors per plate) and incubated for 7 days at 300° C. The cells that have grown on an area of ca. 1 cm$^2$ agar surface are transferred by a plastic loop to 10 ml of G52 medium in a 50 ml Erlenmeyer flask and incubated for 7 days at 180 rpm in an agitator at 30° C. 5 ml of this culture are transferred to 50 ml of G52 medium (in a 200 ml Erlenmeyer flask) and incubated at 180 rpm for 3 days in an agitator at 30° C. 10 ml of this culture are transferred to 50 ml of 23B3 medium and incubated for 7 days at 180 rpm in an agitator at 30° C.

To determine the amounts of epothilone A and epothilone B formed in this culture, the following procedure is followed. The 50 ml culture solution is filtered through a nylon sieve (150 μm pore size), and the polystyrene resin Amberlite XAD16 retained on the sieve is rinsed with a little water and subsequently added together with the filter to a 50 ml centrifuge tube (Falcon Labware, Becton Dickinson AG Immengasse 7, 4056 Basle). 10 ml of isopropanol (>99%) are added to the tube with the filter. Afterwards, the well-sealed tube is shaken for 1 hour at 180 rpm in order dissolve the epothilone A and B, which is bonded to the resin, in the isopropanol. Subsequently, 1.5 ml of the liquid is centrifuged, and ca. 0.8 ml of the supernatant is added using a pipette to a HPLC tube. The HPLC analysis of these samples is effected as described below under HPLC analysis in the product analysis section. The HPLC analysis determines which culture contains the highest content of epothilone B. From the above-described sector plate of the corresponding colony (the plates have been stored at 4° C. in the meantime), cells from ca. 1 cm$^2$ of agar area are transferred by a plastic loop to 10 ml of G52 medium in a 50 ml Erlenmeyer flask and are incubated for 7 days at 180 rpm in an agitator at 30° C. 5 ml of this culture are transferred to 50 ml of G52 medium (in a 200 ml Erlenmeyer flask) and incubated at 180 rpm for 3 days in an agitator at 30° C.

Second and Third UV Mutation Step and Selection

The procedure is exactly the same as described above for the first UV mutation step, whereby the selected culture of the best colony from the first UV mutation is used for the second mutagenesis. For the third mutagenesis, the culture of the best colony from the second mutagenesis is used accordingly. The best colony after this third cycle of UV mutation steps, followed by selection of the resulting strains for improved epothilone B production, corresponds to mutant BCE33/10.

The strain BCE 63/114 is obtained from another (fourth) mutation step from the strain BCE33/10, which is carried out in exactly the same way as the above-mentioned mutation steps.

Preservation of the Strain 10 ml of a 3 day old culture in G52 medium (50 ml medium in a 200 ml Erlenmeyer flask, 30° C. and 180 rpm) are transferred to 50 ml of 23B3 medium (in a 200 ml Erlenmeyer flask) and incubated for 3 days at 180 rpm in an agitator at 30° C. 1 ml portions of this culture are removed in a form which is as homogeneous as possible (prior to each removal the culture is shaken by hand in the Erlenmeyer flask) together with the polystyrene resin Amberlite XAD16 (polystyrene adsorption resin, Rohm & Haas, Frankfurt, Germany), then filled into 1.8 ml Nunc cryotubes (A/S Nunc, DK 4000 Roslide, Denmark) and stored either at −70° C. or in liquid nitrogen.

Cultivation of the strains from these ampoules is effected by heating them in the air to room temperature, and subsequently transferring the entire content of the cryotube to 10 ml G52 medium in an 50 ml Erlenmeyer flask and incubating for 5–7 days at 180 rpm in an agitator at 30° C.

Media

| G52 Medium: | yeast extract, low in salt (Springer, Maison Alfort, France) | 2 g/l |
|---|---|---|
| | $MgSO_4$ (7 $H_2O$) | 1 g/l |
| | $CaCl_2$ (2 $H_2O$) | 1 g/l |
| | soya meal defatted (Mucedola S.r.I., Settimo Milan, Italy) | 2 g/l |
| | potato starch Noredux (Blattmann, Wadenswil, Switzerland) | 8 g/l |
| | glucose anhydrous | 2 g/l |
| | Fe-EDTA 8 g/l (Product No. 03625, Fluka Chemie AG, CH) | 1 ml/l |
| | pH 7.4, corrected with KOH | |
| | Sterilisation: 20 mins. 120° C. | |

S42 Agar-Medium

As described S. Jaoua et al. Plasmid 28, 157–165 (1992)

| 23B3 Medium: | glucose | 2 g/l |
|---|---|---|
| | potato starch Noredux (Blattmann, Wadenswil, Switzerland) | 20 g/l |
| | soya meal defatted (Mucedola S.r.I., Settimo Milan, Italy) | 16 g/l |
| | Fe-EDTA (Product No. 03625, Fluka, Buchs, Switzerland) | 0.008 g/l |
| | HEPES Fluka, Buchs, Switzerland | 5 g/l |
| | polystyrene resin XAD16 (Rohm and Haas) 2% v/v | |
| | $H_2O$ deionised | |
| | correction of pH to 7.8 with NaOH | |
| | sterilisation for 20 mins. at 120° C. | |

(HEPES=4-(2-hydroxyethyl)-piperazine-1-ethanesulfonic acid)

EXAMPLE 2

Cultivation in Order to Produce the Epothilones Strain *Sorangium cellulosum* Soce-90 BCE 33/10

(Example 1)

Preservation of the Strain

In liquid $N_2$, as in Example 1.

| Media: | Precultures and intermediate cultures: | G52 |
|---|---|---|
| | Main culture: | 1B12 |
| | G52 Medium: | |
| | yeast extract, low in salt (BioSpringer, Maison Alfort, France) | 2 g/l |
| | $MgSO_4$ (7 $H_2O$) | 1 g/l |
| | $CaCl_2$ (2 $H_2O$) | 1 g/l |
| | soya meal defatted Soyamine 50T (Lucas Meyer, Hamburg, Germany) | 2 g/l |
| | potato starch Noredux A-150 (Blattmann, Waedenswil, Switzerland) | 8 g/l |
| | glucose anhydrous | 2 g/l |
| | EDTA-Fe(III)-Na salt (8 g/l) | 1 ml/l |
| | pH 7.4, corrected with KOH | |
| | Sterilisation: 20 mins. 120° C. | |
| | 1B12 Medium: | |
| | potato starch Noredux A-150 (Blattmann, Waedenswil, Switzerland) | 20 g/l |
| | soya meal defatted Soyamine 50T (Lucas Meyer, Hamburg, Germany) | 11 g/l |
| | EDTA-Fe(III)-Na salt | 8 mg/l |
| | pH 7.8, corrected with KOH | |
| | Sterilisation: 20 mins. 120° C. | |
| | Addition of cyclodextrins and cyclodextrin derivatives: | |
| | Cyclodextrins (Fluka, Buchs, Switzerland, or Wacker Chemie, Munich, Germany) in different concentrations are sterilised separately and added to the 1B12 medium prior to seeding. | |

Cultivation 1 ml of the suspension of *Sorangium cellulosum* Soce-90 BCE 33/10 from a liquid $N_2$ ampoule is transferred to 10 ml of G52 medium (in a 50 ml Erlenmeyer flask) and incubated for 3 days at 180 rpm in an agitator at 30° C., 25 mm displacement. 5 ml of this culture is added to 45 ml of G52 medium (in a 200 ml Erlenmeyer flask) and incubated for 3 days at 180 rpm in an agitator at 30° C., 25 mm displacement. 50 ml of this culture is then added to 450 ml of G52 medium (in a 2 liter Erlenmeyer flask) and incubated for 3 days at 180 rpm in an agitator at 30° C., 50 mm displacement.

Maintenance Culture

The culture is overseeded every 3–4 days, by adding 50 ml of culture to 450 ml of G52 medium (in a 2 liter Erlenmeyer flask). All experiments and fermentations are carried out by starting with this maintenance culture.

Tests in a Flask (I) Preculture in an Agitating Flask

Starting with the 500 ml of maintenance culture, 1×450 ml of G52 medium are seeded with 50 ml of the maintenance culture and incubated for 4 days at 180 rpm in an agitator at 30° C., 50 mm displacement.

(ii) Main Culture in the Agitating Flask 40 ml of 1B12 medium plus 5 g/l 4-morpholine-propane-sulfonic acid (=MOPS) powder (in a 200 ml Erlenmeyer flask) are mixed with 5 ml of a 10× concentrated cyclodextrin solution, seeded with 10 ml of preculture and incubated for 5 days at 180 rpm in an agitator at 30° C., 50 mm displacement.

Fermentation

Fermentations are carried out on a scale of 10 liters, 100 liters and 500 liters. 20 liter and 100 liter fermentations serve as an intermediate culture step. Whereas the precultures and intermediate cultures are seeded as the maintenance culture 10% (v/v), the main cultures are seeded with 20% (v/v) of the intermediate culture. Important: In contrast to the agitating cultures, the ingredients of the media for the fermentation are calculated on the final culture volume including the inoculum. If, for example, 18 liters of medium+2 liters of inoculum are combined, then substances for 20 liters are weighed in, but are only mixed with 18 liters!

Preculture in an Agitating Flask

Starting with the 500 ml maintenance culture, 4×450 ml of G52 medium (in a 2 liter Erlenmeyer flask) are each seeded with 50 ml thereof, and incubated for 4 days at 180 rpm in an agitator at 30° C., 50 mm displacement.

Intermediate Culture, 20 Liters or 100 Liters 20 liters: 18 liters of G52 medium in a fermenter having a total volume of 30 liters are seeded with 2 liters of the preculture. Cultivation lasts for 3–4 days, and the conditions are: 30° C., 250 rpm, 0.5 liters air per liter liquid per min, 0.5 bars excess pressure, no pH control.

100 liters: 90 liters of G52 medium in a fermenter having a total volume of 150 liters are seeded with 10 liters of the 20 liter intermediate culture. Cultivation lasts for 3–4 days, and the conditions are: 30° C., 150 rpm, 0.5 liters of air per liter liquid per min, 0.5 bars excess pressure, no pH control.

Main Culture, 10 Liters, 100 Liters or 500 Liters 10 liters: The media substances for 10 liters of 1B12 medium are sterilised in 7 liters of water, then 1 liter of a sterile 10% 2-(hydroxypropyl)-0-cyclodextrin solution are added, and seeded with 2 liters of a 20 liter intermediate culture. The duration of the main culture is 6–7 days, and the conditions are: 30° C., 250 rpm, 0.5 liters of air per liter of liquid per min, 0.5 bars excess pressure, pH control with $H_2SO_4$/KOH to pH 7.6+/−0.5 (i.e. no control between pH 7.1 and 8.1).

100 liters: The media substances for 100 liters of 1B12 medium are sterilised in 70 liters of water, then 10 liters of a sterile 10% 2-(hydroxypropyl)-β-cyclodextrin solution are added, and seeded with 20 liters of a 20 liter intermediate culture. The duration of the main culture is 6–7 days, and the conditions are: 30° C., 200 rpm, 0.5 liters air per liter liquid per min., 0.5 bars excess pressure, pH control with $H_2SO_4$KOH to pH 7.6+/−0.5. The chain of seeding for a 100 liter fermentation is shown schematically as follows:

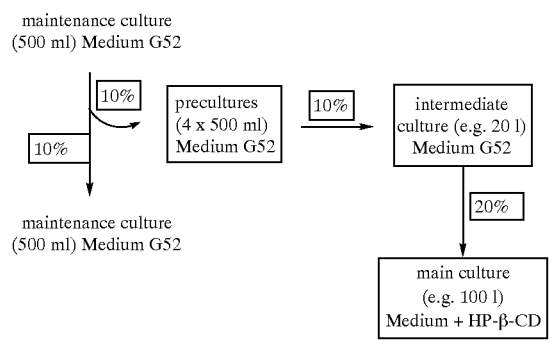

500 liters: The media substances for 500 liters of 1B12 medium are sterilised in 350 liters of water, then 50 liters of a sterile 10% 2-(hydroxypropyl)-β-cyclodextrin solution are added, and seeded with 100 liters of a 100 liter intermediate culture. The duration of the main culture is 6–7 days, and the conditions are: 30° C., 120 rpm, 0.5 liters air per liter liquid per min, 0.5 bars excess pressure, pH control with $H_2SO_4$/KOH to pH 7.6+/−0.5.

Product Analysis

Preparation of the Sample 50 ml samples are mixed with 2 ml of polystyrene resin Amberlite XAD16 (Rohm+Haas, Frankfurt, Germany) and shaken at 180 rpm for one hour at 30° C. The resin is subsequently filtered using a 150 μm nylon sieve, washed with a little water and then added together with the filter to a 15 ml Nunc tube.

Elution of the Product From the Resin 10 ml of isopropanol (>99%) are added to the tube with the filter and the resin. Afterwards, the sealed tube is shaken for 30 minutes at room temperature on a Rota-Mixer (Labinco BV, Netherlands). Then, 2 ml of the liquid are centrifuged off and the supernatant is added using a pipette to HPLC tubes.

| HPLC analysis: | |
|---|---|
| Column: | Waters-Symetry C18, 100 × 4 mm, 3.5 μm WAT066220 + preliminary column 3.9 × 20 mm WAT054225 |
| Solvents: | A: 0.02% phosphoric acid B: Acetonitrile (HPLC-Quality) |
| Gradient: | 41% B from 0 to 7 min. 100% B from 7.2 to 7.8 min. 41% B from 8 to 12 min. |
| Oven temp.: | 30° C. |
| Detection: | 250 nm, UV-DAD detection |
| Injection vol.: | 10 μl |
| Retention time: | Epo A: 4.30 min Epo B: 5.38 min |

EXAMPLE 2A

Effect of the Addition of Cyclodextrin and Cyclodextrin Derivatives to the Epothilone Concentrations Attained All the cyclodextrin derivatives tested here come from the company Fluka, Buchs, CH. The tests are carried out in 200 ml agitating flasks with 50 ml culture volume. As controls, flasks with adsorber resin Amberlite XAD-16 (Rohm & Haas, Frankfurt, Germany) and without any adsorber addition are used. After incubation for 5 days, the following epothilone titres can be determined by HPLC:

TABLE 1

| Addition | order No. | Conc [% w/v][1] | Epo A [mg/l] | Epo B [mg/l] |
|---|---|---|---|---|
| Amberlite XAD-16 (v/v) | | 2.0 (% v/v) | 9.2 | 3.8 |
| 2-hydroxypropyl-β-cyclodextrin | 56332 | 0.1 | 2.7 | 1.7 |
| 2-hydroxypropyl-β-cyclodextrin | " | 0.5 | 4.7 | 3.3 |
| 2-hydroxypropyl-β-cyclodextrin | " | 1.0 | 4.7 | 3.4 |
| 2-hydroxypropyl-β-cyclodextrin | " | 2.0 | 4.7 | 4.1 |
| 2-hydroxypropyl-β-cyclodextrin | " | 5.0 | 1.7 | 0.5 |
| 2-hydroxypropyl-α-cyclodextrin | 56330 | 0.5 | 1.2 | 1.2 |
| 2-hydroxypropyl-α-cyclodextrin | " | 1.0 | 1.2 | 1.2 |
| 2-hydroxypropyl-α-cyclodextrin | " | 5.0 | 2.5 | 2.3 |
| β-cyclodextrin | 28707 | 0.1 | 1.6 | 1.3 |
| β-cyclodextrin | " | 0.5 | 3.6 | 2.5 |
| β-cyclodextrin | " | 1.0 | 4.8 | 3.7 |
| β-cyclodextrin | " | 2.0 | 4.8 | 2.9 |
| β-cyclodextrin | " | 5.0 | 1.1 | 0.4 |
| methyl-β-cyclodextrin | 66292 | 0.5 | 0.8 | <0.3 |
| methyl-β-cyclodextrin | " | 1.0 | <0.3 | <0.3 |
| methyl-β-cyclodextrin | " | 2.0 | <0.3 | <0.3 |
| 2,6 di-o-methyl-β-cyclodextrin | 39915 | 1.0 | <0.3 | <0.3 |
| 2-hydroxypropyl-γ-cyclodextrin | 56334 | 0.1 | 0.3 | <0.3 |
| 2-hydroxypropyl-γ-cyclodextrin | " | 0.5 | 0.9 | 0.8 |
| 2-hydroxypropyl-γ-cyclodextrin | " | 1.0 | 1.1 | 0.7 |
| 2-hydroxypropyl-γ-cyclodextrin | " | 2.0 | 2.6 | 0.7 |

TABLE 1-continued

| Addition | order No. | Conc [% w/v][1] | Epo A [mg/l] | Epo B [mg/l] |
|---|---|---|---|---|
| 2-hydroxypropyl-γ-cyclodextrin | " | 5.0 | 5.0 | 1.1 |
| no addition | | | 0.5 | 0.5 |

[1]) Apart from Amberlite (% v/v), all percentages are by weight (% w/v).

Few of the cyclodextrins tested (2,6-di-o-methyl-β-cyclodextrin, methyl-β-cyclodextrin) display no effect or a negative effect on epothilone production at the concentrations used. 1–2% 2-hydroxy-propyl-β-cyclodextrin and β-cyclodextrin increase epothilone production in the examples by 6 to 8 times compared with production using no cyclodextrins.

EXAMPLE 2B
10 Liter Fermentation With 1% 2-(hydroxypropyl)-β-cyclodextrin)

Fermentation is carried out in a 15 liter glass fermenter. The medium contains 10 g/l of 2-(hydroxypropyl)-β-cyclodextrin from Wacker Chemie, Munich, Germany. The progress of fermentation is illustrated in Table 2. Fermentation is ended after 6 days and working up takes place.

TABLE 2

Progress of a 10 liter fermentation

| duration of culture [d] | Epo A [mg/l] | Epo B [mg/l] |
|---|---|---|
| 0 | 0 | 0 |
| 1 | 0 | 0 |
| 2 | 0.5 | 0.3 |
| 3 | 1.8 | 2.5 |
| 4 | 3.0 | 5.1 |
| 5 | 3.7 | 5.9 |
| 6 | 3.6 | 5.7 |

EXAMPLE 2C
100 Liter Fermentation With 1% 2-(hydroxypropyl)-β-cyclodextrin)

Fermentation is carried out in a 150 liter fermenter. The medium contains 10 g/l of 2-(hydroxypropyl)-β-cyclodextrin. The progress of fermentation is illustrated in Table 3. The fermentation is harvested after 7 days and worked up.

TABLE 3

Progress of a 100 liter fermentation

| duration of culture [d] | Epo A [mg/l] | Epo B [mg/l] |
|---|---|---|
| 0 | 0 | 0 |
| 1 | 0 | 0 |
| 2 | 0.3 | 0 |
| 3 | 0.9 | 1.1 |
| 4 | 1.5 | 2.3 |
| 5 | 1.6 | 3.3 |
| 6 | 1.8 | 3.7 |
| 7 | 1.8 | 3.5 |

EXAMPLE 2D
500 Liter Fermentation With 1% 2-(hydroxypropyl)-β-cyclodextrin)

Fermentation is carried out in a 750 liter fermenter. The medium contains 10 g/l of 2-(hydroxypropyl)-β-cyclodextrin. The progress of fermentation is illustrated in Table 4. The fermentation is harvested after 7 days and worked up.

TABLE 4

Progress of a 500 liter fermentation

| duration of culture [d] | Epo A [mg/l] | Epo B [mg/l] |
|---|---|---|
| 0 | 0 | 0 |
| 1 | 0 | 0 |
| 2 | 0 | 0 |
| 3 | 0.6 | 0.6 |
| 4 | 1.7 | 2.2 |
| 5 | 3.1 | 4.5 |
| 6 | 3.1 | 5.1 |

EXAMPLE 2E
Comparison Example 10 Liter Fermentation Without Adding an Adsorber Fermentation is carried out in a 15 liter glass fermenter. The medium does not contain any cyclodextrin or other adsorber. The progress of fermentation is illustrated in Table 5. The fermentation is not harvested and worked up.

TABLE 5

Progress of a 10 liter fermentation without adsorber.

| duration of culture [d] | Epothilone A [mg/l] | Epothilone B [mg/l] |
|---|---|---|
| 0 | 0 | 0 |
| 1 | 0 | 0 |
| 2 | 0 | 0 |
| 3 | 0 | 0 |
| 4 | 0.7 | 0.7 |
| 5 | 0.7 | 1.0 |
| 6 | 0.8 | 1.3 |

EXAMPLE 3
Working Up of the Epothilones: Isolation From a 500 Liter Main Culture The volume of harvest from the 500 liter main culture of example 2D is 450 liters and is separated using a Westfalia clarifying separator Type SA-20-06 (rpm=6500) into the liquid phase (centrifugate+rinsing water=650 liters) and solid phase (cells=ca. 15 kg). The main part of the epothilones are found in the centrifugate. The centrifuged cell pulp contains <15% of the determined epothilone portion and is not further processed. The 650 liter centrifugate is then placed in a 4000 liter stirring vessel, mixed with 10 liters of Amberlite XAD-16 (Centrifugate:resin volume= 65:1) and stirred. After a period of contact of ca. 2 hours, the resin is centrifuged away in a Heine overflow centrifuge (basket content 40 liters; rpm=2800). The resin is discharged from the centrifuge and washed with 10–15 liters of deionised water. Desorption is effected by stirring the resin twice, each time in portions with 30 liters of isoprapopanol in 30 liter glass stirring vessels for 30 minutes. Separation of the isopropanol phase from the resin takes place using a suction filter. The isopropanol is then removed from the combined isopropanol phases by adding 15–20 liters of water in a vacuum-operated circulating evaporator (Schmid-Verdampfer) and the resulting water phase of ca. 10 liters is extracted 3× each time with 10 liters of ethyl acetate. Extraction is effected in 30 liters glass stirring vessels. The ethyl acetate extract is concentrated to 3–5 liters in a vacuum-operated circulating evaporator (Schmid-Verdampfer) and afterwards concentrated to dryness in a rotary evaporator (Büchi type) under vacuum. The result is an ethyl acetate extract of 50.2 g. The ethyl acetate extract is dissolved in 500 ml of methanol, the insoluble portions filtered off using a folded filter, and the solution added to a 10 kg Sephadex LH 20 column (Pharmacia, Uppsala, Sweden) (column diameter 20 cm, filling level ca. 1.2 m). Elution is effected with methanol as eluant. Epothilone A and B is present predominantly in fractions 21–23 (at a fraction size of 1 liter). These fractions are concentrated to dryness in a vacuum on a rotary evaporator (total weight 9.0 g). These Sephadex peak fraction (9.0 g) are thereafter dissolved in 92 ml of acetonitrile:water:methylene chloride= 50:40:2, the solution filtered through a folded filter and added to a RP column (equipment Prepbar 200, Merck; 2.0 kg LiChrospher RP-18 Merck, grain size 12μm, column diameter 10 cm, filling level 42 cm; Merck, Darmstadt, Germany). Elution is effected with acetonitrile:water=3:7 (flow rate=500 ml/min.; retention time of epothilone A=ca. 51–59 mins.; retention time of epothilone B=ca. 60–69 mins.). Fractionation is monitored with a UV detector at 250 nm. The fractions are concentrated to dryness under vacuum on a Büchi-Rotavapor rotary evaporator. The weight of the epothilone A peak fraction is 700 mg, and according to HPLC (external standard) it has a content of 75.1%. That of the epothilone B peak fraction is 1980 mg, and the content according to HPLC (external standard) is 86.6%. Finally, the epothilone A fraction (700 mg) is crystallised from 5 ml of ethyl acetate:toluene=2:3, and yields 170 mg of epothilone A pure crystallisate [content according to HLPC (% of area)=94.3%]. Crystallisation of the epothilone B fraction (1980 mg) is effected from 18 ml of methanol and yields 1440 mg of epothilone B pure crystallisate [content according to HPLC (%) of area=99.2%]. m.p. (Epothilone B): 124–125° C.; $^1$H-NMR data for Epothilone B: 500 MHz-NMR, solvent: DMSO-d6. Chemical displacement δ in ppm relative to TMS. s=singlet; d=doublet; m=multiplet

| δ (Multiplicity) | Integral (number of H) |
|---|---|
| 7.34 (s) | 1 |
| 6.50 (s) | 1 |
| 5.28 (d) | 1 |
| 5.08 (d) | 1 |
| 4.46 (d) | 1 |
| 4.08 (m) | 1 |
| 3.47 (m) | 1 |
| 3.11 (m) | 1 |
| 2.83 (dd) | 1 |
| 2.64 (s) | 3 |
| 2.36 (m) | 2 |
| 2.09 (s) | 3 |
| 2.04 (m) | 1 |
| 1.83 (m) | 1 |
| 1.61 (m) | 1 |
| 1.47–1.24 (m) | 4 |
| 1.18 (s) | 6 |
| 1.13 (m) | 2 |
| 1.06 (d) | 3 |
| 0.89 (d + s, overlapping) | 6 |
| Σ = 41 | |

In this example (Example 3), epothilone B is obtained in the crystal modification A, which is characterised by the X-ray diffraction diagram of modification A (see general part of the present disclosure).

EXAMPLE 4

Crystal Modification B of Epothilone B 50 mg of epothilone B (obtained for example as above) are suspended in 1 ml of isopropanol and shaken for 24 hours at 25° C. The product is filtered and dried. After drying under a high vacuum, epothilones B are obtained in the form of white crystals. The crystal modification of the product is characterised by the X-ray diffraction diagram of modification B (see general part of the present disclosure).

EXAMPLE 5

3000 Liter Fermentation With 2-(hydroxypropyl)-β-cyclodextrin)

Fermentation is carried out with the strain BCE 63/114 in a 5000 liter fermenter in 1B12 medium (filled volume 3000 liters).

Maintenance culture: Preparation is effected as described in Example 1 (strain preservation) and 2 for the strain BCE33/10, but using instead the strain BCE63/114.

Precultures

Preparation of the precultures is effected analogously to Example 2 (ii), but with the following precultures and with strain BCE 63/114:

From a 500 ml maintenance culture [as described in example 2 (ii)], 50 ml portions are placed in 4 Erlenmeyer flasks, thus producing four 500 ml precultures in G52 medium for 3 days at 30° C. and at 180 rpm. These 4 precultures (2 liters) are then used for three intermediate cultures each of 20 liters (G52 medium, 4 days, 30° C., 250 rpm). 5 liter portions of these intermediate cultures are used to produce three 50 liter intermediate cultures (G52 medium, 3 days, 30° C., 200 rpm). 50 liters of these 50 liter intermediate cultures are used twice to grow two 600 liter intermediate cultures (G52 medium, 4 days, 30° C., 120 rpm).

Main Culture

The media substances for 3000 liters are sterilised in 2100 liters of water, then 300 liters of a sterile 10% 2-(hydroxypropyl)-β-cyclodextrin solution are added, and seeded with 600 liters of an intermediate culture. The duration of the main culture is 6–7 days, and the conditions are: 30° C., 100 rpm, 0.5 liters of air per liter liquid per minute, 0.5 bars excess pressure, pH control with $H_2SO_4$/KOH to pH 7.6+/−0.5 (i.e. no control between pH 7.1 and 8.1). The progress of fermentation is illustrated in Table 6.

TABLE 6

Progress of a 3000 liter fermentation

| duration of culture [d] | Epothilone A [mg/l] | Epothilone B [mg/l] |
|---|---|---|
| 0 | 0 | 0 |
| 1 | 0 | 0 |
| 2 | 0 | 0 |
| 3 | 2.1 | 1.6 |
| 4 | 4.1 | 2.9 |
| 5 | 5.2 | 3.8 |
| 6 | 5.5 | 4.3 |

Working Up and Isolation of the Epothilones From a 3000 Liter Main Culture (I) Resin Binding, Desorption and Extraction of the Epothilones (Ethyl Acetate Extract)

The volume of harvest from the 3000 liter main culture is 2900 liters and is separated using a Westfalia clarifying separator Type SA-20-06 (rpm=6500, flow rate 1400 liters/hour) into the liquid phase (centrifugate+rinsing water=2750 liters) and solid phase (cells=ca. 260 kg). The main part of the epothilones are found in the centrifugate. The centrifuged cell pulp contains <15% of the determined epothilone portion and is not further processed. The 2750 liter centrifugate is then placed in a 4000 liter steel stirring vessel, mixed with 60 liters of Amberlite SAD-16 (centrifugate:resin volume=46:1) and stirred. After a period of contact of 16–20 hours, the resin is centrifuged away in a Heine overflow centrifuge (basket content 40 liters; rpm=2800). The centrifuge is emptied by rinsing the basket content with deionised water when the centrifuge is stationary. The XAD-16/deionised water slurry is thereafter freed from water on a suction filter (Ø50 cm) and the resin washed with 30 liters of deionised water. Desorption of the resin is effected by stirring it in a 1600 liter stirring vessel twice, each time with 220 liters of isopropanol for 30 minutes. Separation of the isopropanol phase from the resin takes place using a suction filter (Ø50 cm). The isopropanol is then removed from the isopropanol phase by adding 240–260 liters of water in a vacuum-operated circulating evaporator (Schmid-Verdampfer) and the resulting water phase of ca. 125 liters is extracted 3× each time with 100–125 liters of ethyl acetate. Extraction is effected in 1600 liter steel stirring vessels. The ethyl acetate extracts are combined, concentrated to 3–5 liters in vacuum-operated circulating evaporators (Büchi Verdampfer/Schmid-Verdampfer) and afterwards concentrated to dryness in a rotary evaporator (Büchi type) under vacuum. An ethyl acetate extract of 590 g is obtained.

HPLC Purification of the Ethyl Acetate Extract (Separation of Epothilones A and B)

Ca. 300 g of the above-mentioned ethyl acetate extract (with a content of ca. 1–1.5% epothilone B) are suspended in 1.5 liters of acetonitrile/water=3/1 (v/v), the solution is filtered through a folded filter and the filtrate added to a C-18 RP column [Prochrom apparatus with 30 cm internal column diameter (Prochrom, Champigneulles, France) 25 kg YMC gel, ODS-A, 120 Angstroem pore diameter, 5–15 μm grain size, spherical]. Elution is effected with acetonitrile/water=4/6 (v/v) at a flow rate of 2300 ml/min. Fractionation is monitored by means of on-line HPLC [rapid HPLC at high temperatures (ca. 80° C.), on a short separating column (4.6 mm internal diameter×75 mm length) and very small RP-18 particles (3.5 μm spherical), typical analysis times are <1 minute, detection at 250 nm]. The valuable fractions (those with only epothilone B) are combined, the acetonitrile removed by distillation and the aqueous phase extracted twice with isopropyl acetate. The organic phases are concentrated by distillation and the isopropyl acetate extract is obtained as the residue of evaporation.

(iii) Silica Gel Filtration of the Isopropyl Acetate Extract

Ca. 10 g of the combined residues of evaporation thus obtained (with a content of ca. 23% of epothilone B) are dissolved at room temperature in 360 ml of ethyl acetate, the solution is filtered through a folded filter and added to a column of silica gel (Prochrom apparatus with 10 cm internal column diameter, 1.5 kg ICN 18–32 μm). Elution is effected with ethyl acetate/n-hexane=4/1 (v/v) at a flow rate of 250 ml/min at room temperature. Fractionation is monitored with a UV detector at 250 nm. The valuable fractions are combined, the solvent removed by distillation and concentrated to dryness.

(iv) Extraction of the Pure Epothilones

Ca. 48 g of the combined residues obtained under (iii) (with a content of ca. 90% of epothilone B) are dissolved in 1150 ml of methanol, mixed with 14.5 g of activated carbon and subsequently filtered through a folded filter. The clear filtrate is subsequently concentrated to dryness and the residue is recrystallised from 317 ml of methanol. 29.5 g of epothilone B are obtained in a purity of 99.7%, and with a melting point of 124° C.

EXAMPLE 6

Infusion Concentrate

By dissolving in polyethylene glycol PEG 300, crystal modification A of epothilone B, or crystal modification B of epothilone B, is produced in a preconcentrate to produce infusion solutions, and stored in vials.

What is claimed is:

1. A process for producing epothilones in a culture medium for the biotechnological preparation of these compounds, the process comprising
   (a) providing microorganisms which produce these compounds in the medium, and
   (b) adding a complex-forming component which is soluble in the culture medium to the medium and forms complex with the compounds.

2. A process according to claim 1 wherein said microorganisms are myxobacteria.

3. A process according to claim 1, in which
   (a) a culture medium is used for the biotechnological preparation of epothilones, said culture medium containing a Sorangium strain suitable for the preparation thereof, water and other suitable customary components of culture media, and
   (b) one or more cyclodextrins are added to the medium as complex-forming component, the cyclodextrins being selected from α-cyclodextrin, β-cyclodextrin, γ-cyclodextrin, δ-cyclodextrin, ε-cyclodextrin, ζ-cyclodextrin, η-cyclodextrin and θ-cyclodextrin; or a cyclodextrin derivative or a mixture of cyclodextrin derivatives selected from derivatives of a cyclodextrin in which one or more up to all of the hydroxy groups are etherified to an alkyl ether, an aryl-hydroxyalkyl ether; a hydroxyalkyl ether; a carboxyalkyl ether; a derivatized carboxy lower alkyl ether in which the derivatized carboxy is aminocarbonyl, mono- or di-lower-alkylaminocarbonyl, morpholino-, piperidino-, pyrrolidino- or piperazino-carbonyl, or alkyloxycarbonyl; a sulfoalkyl ether; a cyclodextrin in which one or more OH groups are etherified with a radical of formula

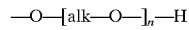

wherein alk is alkyl and n is a whole number from and including 2 up to and including 12; a cyclodextrin in which one or more OH groups are etherified with a radical of formula

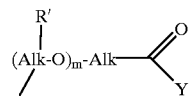

wherein R' is hydrogen, hydroxy, —O—(alk—O)$_z$—H, —O—(alk(—R)—O—)$_p$—H or —O—(alk(—R)—O—)$_q$—alk—CO—Y; alk in all cases is alkyl; m, n, p, q and z are a whole number from 1 to 12; and Y is OR$_1$ or NR$_2$R$_3$, wherein R$_1$, R$_2$ and R$_3$, independently of one another, are hydrogen or lower alkyl, or R$_2$ and R$_3$, combined with the binding nitrogen signify morpholino, piperidino, pyrrolidino or piperazino; or a branched cyclodextrin in which etherifications or acetals exist with other sugar molecules, and which are selected from glucosyl-, diglucosyl-(G$_2$-β- cyclodextrin), maltosyl- and dimaltosyl-cyclodextrin, or N-acetylglucosaminyl-, glucosaminyl-, N-acetylgalactosaminyl- and galactosaminyl-cyclodextrin; and a lower alkanoyl-, such as acetylester of a cyclodextrin; or mixtures of two or more of the said cyclodextrins and/or cyclodextrin derivatives.

4. Process according to claim 3, in which the cyclodextrin and/or the cyclodextrin derivative is added to the culture medium in a concentration of between 0.05 and 10 percent by weight (w/v).

5. Process according to claim 4, in which the cyclodextrin and/or the cyclodextrin derivative is added in a concentration of between 0.1 and 2 percent by weight.

6. A process according to claim 3, in which the cyclodextrin derivative is selected from a cyclodextrin and a hydroxy lower alkyl cyclodextrin; or mixtures of one or more thereof.

7. A process according to claim 1, in which the complex-forming component is 2-hydroxy-propyl-β-cyclodextrin.

8. A process for the production of epothilones, which process comprises providing a culture medium for the biotechnological preparation of these compounds, the medium comprising myxobacteria as producers of natural substances, adding to the medium a complex-forming component which is soluble in the culture medium, and subsequently purifying and, if desired, separating the epothilones from one another, wherein the complex-forming component forms complex with the epothilones.

9. A process according to claim 8, wherein epothilone A and/or epothilone B are obtained from a culture medium for the biotechnological preparation of these compounds comprising a myxobacterium of the genus Sorangium, and to which culture medium is added a complex-forming component which is soluble in the culture medium, comprising separating the culture into the solid and the liquid phase (centrifugate) by centrifugation; mixing the centrifugate with a resin or running it over a column filled with such a resin; if necessary washing the resin with water; desorbing the epothilone(s) from the resin with a polar solvent; if necessary concentrating with prior, simultaneous or subsequent addition of water; adding an organic solvent which is immiscible with water added and transferring the epothilone (s) into the organic phase; concentrating the organic phase obtained if required; concentrating the epothilones from the organic solution obtained are a molecular sieve for compounds of low molecular weight; and subsequently making the fractions containing the epothilones undergo separation on a reversed-phase column; whereby epothilones A and/or B are obtained separately and, if desired, can be further concentrated by recrystallization.

10. A process according to claim 8 for the production of epothilone A and/or B, wherein the epothilones A and/or B are obtained from a culture medium for the biotechnological preparation of these compounds, to which medium is added a complex-forming component which is soluble in the culture medium, comprising separating the culture into the solid and the liquid phase (centrifugate) by centrifugation; mixing the centrifugate with a resin or running it through a column filled with such a resin; if necessary washing the resin with water; desorbing the epothilone(s) from the resin with a polar solvent; if necessary removing the polar solvent with prior, simultaneous or subsequent addition of water; extracting the resulting water phase with a solvent suitable for forming a second phase; concentrating the organic phase obtained if required; separating epothilone A and epothilone B from one another directly by reversed-phase chromatography whilst eluting with an eluent containing a nitrile; concentrating subsequently; if desired, treating the residue from an aqueous solution by extracting once or several times with a solvent which is immiscible with water; dissolving it in an appropriate solvent, filtering the resulting solution if necessary, adding the solution to a silica gel column and eluting with an appropriate solvent or solvent mixture; and subsequently separately combining each fraction containing epothilone A or in particular B and concentrating it by removing the solvent; then dissolving the residue in an appropriate alcohol, if desired, in order to obtain especially high purity, mixing with activated carbon and then filtering; and finally obtaining epothilone A or B by recrystallization.

11. A process for the production of epothilones, which comprising
a) concentrating epothilones in a culture medium for the biotechnological preparation of these compounds, which contains a microorganism suitable for the preparation thereof, water and other suitable customary constituents of culture media, whereby a cyclodextrin or a cyclodextrin derivative is added to the medium, or a mixture of two or more of these compounds; and
b) a step for separating epothilones from one another, which is characterised by chromatography on a reversed-phase column with an eluant comprising a lower alkylcyanide, whereby chromatography is carried out on column material charged with hydrocarbon chains, and an eluant comprising a lower alkyinitrile is used; whereby if desired further working up steps and purification steps are possible.

12. The process of claim 11, wherein the cyclodextrin or derviative thereof is selected from α-cyclodextrin, β-cyclodextrin, γ-cyclodextrin, δ-cyclodextrin, ε-cyclodextrin, ζ-cyclodextrin, η-cyclodextrin and θ-cyclodextrin; or a cyclodextrin derivative or a mixture of cyclodextrin derivatives selected from derivatives of a cyclodextrin in which one or more up to all of the hydroxy groups are etherified to an alkyl ether, an aryl-hydroxyalkyl ether; a hydroxyalkyl ether; a carboxyalkyl ether; a derivatized carboxy lower alkyl ether in which the derivatized carboxy is aminocarbonyl, mono- or di-lower-alkylaminocarbonyl, morpholino-, piperidino-, pyrrolidino- or piperazino-carbonyl, or alkyloxycarbonyl; a sulfoalkyl ether; a cyclodextrin in which one or more OH groups are etherified with a radical of formula

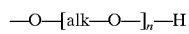

wherein alk is alkyl and n is a whole number from and including 2 up to and including 12; a cyclodextrin in which one or more OH groups are etherified with a radical of formula

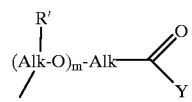

wherein R' is hydrogen, hydroxy, —O—(alk—O)$_z$—H, —O—(alk(—R)—O—)$_p$—H or —O—(alk(—R)—O—)$_q$—alk—CO—Y; alk in all cases is alkyl; m, n, p, q and z are a whole number from 1 to 12; and Y is OR$_1$ or NR$_2$R$_3$, wherein R$_1$, R$_2$ and R$_3$, independently of one another, are hydrogen or lower alkyl, or R$_2$ and R$_3$, combined with the binding nitrogen signify morpholino, piperidino, pyrrolidino or piperazino; or a branched cyclodextrin in which etherifications or acetals exist with other sugar molecules, and which are selected from glucosyl-, diglucosyl-(G$_2$-β- cyclodextrin), maltosyl- and dimaltosyl-cyclodextrin, or N-acetylglucosaminyl-, glucosaminyl-, N-acetylgalactosaminyl- and galactosaminyl-cyclodextrin; and a lower alkanoyl-; or mixtures of two or more of the cyclodextrins.

13. The process of claim 11 wherein the cyclodextrin or derivative thereof is added to the culture medium in a concentration of between 0.05 and 10 percent by weight (w/v).

14. The process of claim 13 wherein the cyclodextrin or derivative thereof is added to the culture medium in a concentration of between 0.1 and 2 percent by weight (w/v).

15. The process of claim 11 wherein the cyclodextrin derivative comprises 2-hydroxy-propyl-$\beta$-cyclodextrin.

* * * * *